United States Patent [19]

Liston et al.

[11] Patent Number: 4,891,104

[45] Date of Patent: Jan. 2, 1990

[54] ENZYMATIC ELECTRODE AND ELECTRODE MODULE AND METHOD OF USE

[75] Inventors: Max D. Liston, Irvine; Paul K. Hsei, Huntington Beach; Christopher C. Feistel, Laguna Beach, all of Calif.

[73] Assignee: SmithKline Diagnostics, Inc., San Jose, Calif.

[21] Appl. No.: 42,266

[22] Filed: Apr. 24, 1987

[51] Int. Cl.$^4$ .......................................... G01N 27/46
[52] U.S. Cl. ..................... 204/1 T; 204/403; 204/415; 73/866.5
[58] Field of Search ...................... 204/1 T, 403, 415; 73/866.5

[56] References Cited

U.S. PATENT DOCUMENTS

| D. 222,237 | 10/1971 | Schmit | D9/194 |
|---|---|---|---|
| 2,805,191 | 9/1957 | Hersch | 204/1 |
| 2,851,654 | 9/1958 | Haddad | 324/30 |
| 2,902,396 | 9/1959 | Reynolds | 154/50 |
| 2,913,386 | 11/1959 | Clark, Jr. | 204/195 |
| 3,056,492 | 10/1962 | Campbell | 206/56 |
| 3,076,592 | 2/1963 | Means et al. | 229/55 |
| 3,098,813 | 7/1963 | Beebe et al. | 204/195 |
| 3,140,196 | 7/1964 | Lacy et al. | 117/75 |
| 3,208,926 | 9/1965 | Eckfeldt et al. | 204/195 |
| 3,259,301 | 7/1966 | Onasch | 229/55 |
| 3,275,534 | 9/1966 | Cannon, Jr. | 204/1 |

(List continued on next page.)

FOREIGN PATENT DOCUMENTS

0078636A1 11/1983 European Pat. Off. .
0125136A2 11/1984 European Pat. Off. .
0125137A2 11/1984 European Pat. Off. .
0125139A2 11/1984 European Pat. Off. .

OTHER PUBLICATIONS

Analyzers with Miniature Solid State Electrodes (Ionetics).
Microchemical Aspects of the AcuChem Microanalyzer (Ortho Diagnostics Instruments).
The YSI Stat Lactate Analyzer (Yellow Springs Instrument Company, Inc.).
Non Diluting Electrolyte Analyzer (NOVA Biomedical).

*Primary Examiner*—Stephen J. Kalafut
*Attorney, Agent, or Firm*—Stetina and Brunda

[57] ABSTRACT

An improved enzymatic electrode and electrode module specifically adapted for use in a medical analyzer device is disclosed which permits rapid analysis of substances of interest contained within undiluted body fluids such as whole blood, serum and/or plasma. The enzymatic electrode is in fluid communication with an axially reciprocating probe which selectively transports either a quantity of a buffer aqueous solution or a calibrant aqueous solution presented at a wash cell or a body fluid specimen disposed within a sample cup to an active enzyme bearing membrane positioned adjacent the enzymatic electrode. The membrane comprises a composite membrane structure having a protective membrane layer adapted to prevent the passage of blood cells and other particulate or cellular substances therethrough as well as adjust the diffusion rate of the substance of interest desired to be measured into the membrane, an active enzyme layer adapted to convert the desired substance of interest to be measured into a detectable substance and a limiting membrane formed to prevent the passage of interfering low molecular weight substance therethrough. The membrane/reagent chemistry kinetics of the enzymatic electrode are specifically defined to enable a novel pseudo-rate/created peak measurement technique to be utilized which reduces measurement inaccuracies as well as signal data processing requirements. The membrane/electrode support structure and membrane/electrode solution flow path are specifically formed to permit rapid replacement of the composite membrane and aqueous solutions by non-professional personnel.

44 Claims, 7 Drawing Sheets

Microfiche Appendix Included
(2 Microfiche, 111 Pages)

U.S. PATENT DOCUMENTS

| Number | Date | Name | Class |
|---|---|---|---|
| 3,294,652 | 12/1966 | Banks et al. | 204/1 |
| 3,296,113 | 1/1967 | Hansen | 204/195 |
| 3,334,039 | 8/1967 | Vlasak | 204/195 |
| 3,367,849 | 2/1968 | Blaedel et al. | 204/1 |
| 3,380,905 | 4/1968 | Clark, Jr. | 204/195 |
| 3,382,105 | 5/1968 | McBryar et al. | 136/86 |
| 3,438,567 | 4/1969 | Bell, Jr. | 229/57 |
| 3,445,365 | 5/1969 | Ross | 204/195 |
| 3,479,255 | 11/1969 | Arthur | 204/1 |
| 3,539,455 | 11/1970 | Clark, Jr. | 204/1 |
| 3,542,662 | 11/1970 | Hicks et al. | 204/195 |
| 3,562,129 | 2/1971 | Simon | 294/296 |
| 3,575,836 | 4/1971 | Sternberg | 204/195 |
| 3,671,460 | 11/1971 | Krull et al. | 204/195 |
| 3,707,455 | 12/1972 | Derr et al. | 204/195 |
| 3,712,848 | 1/1973 | Casey, Jr. et al. | 161/213 |
| 3,718,563 | 2/1973 | Krull et al. | 204/195 |
| 3,719,086 | 3/1973 | Bannister et al. | 73/423 A |
| 3,776,819 | 12/1973 | Williams | 204/1 |
| 3,799,914 | 3/1974 | Schmit et al. | 426/85 |
| 3,838,033 | 9/1974 | Mindt et al. | 204/195 |
| 3,840,452 | 10/1974 | Baum et al. | 204/195 |
| 3,856,649 | 12/1974 | Genshaw et al. | 204/195 F |
| 3,857,777 | 12/1974 | Guilbault et al. | 204/296 |
| 3,864,233 | 2/1975 | Dietrich et al. | 204/195 |
| 3,869,354 | 3/1975 | Montalve, Jr. | 204/195 |
| 3,911,749 | 10/1975 | Hendry | 73/423 A |
| 3,919,071 | 11/1975 | Mosé | 204/286 |
| 3,923,626 | 12/1975 | Niedrach et al. | 204/195 R |
| 3,926,764 | 12/1975 | Ruzicka et al. | 204/195 F |
| 3,926,766 | 12/1975 | Ruzicka et al. | 204/195 P |
| 3,930,493 | 1/1976 | Williamson | 128/2.05 F |
| 3,957,607 | 5/1976 | Simon et al. | 204/180 |
| 3,979,274 | 9/1976 | Newman | 204/195 |
| 4,073,713 | 2/1978 | Newman | 204/195 |
| 4,115,209 | 9/1978 | Freiser et al. | 204/195 |
| 4,172,770 | 10/1979 | Semersky et al. | 204/1 T |
| 4,284,672 | 5/1981 | Stillman | 428/35 |
| 4,310,400 | 1/1982 | Mark, Jr. et al. | 204/195 M |
| 4,340,457 | 7/1982 | Kater | 204/195 |
| 4,349,429 | 9/1982 | Rhodes et al. | 204/299 R |
| 4,383,451 | 5/1983 | Chapel | 73/864.41 |
| 4,387,126 | 6/1983 | Rebholz | 428/35 |
| 4,418,148 | 11/1983 | Oberhardt | 204/403 |
| 4,473,458 | 9/1984 | Schwartz et al. | 204/433 |
| 4,490,235 | 12/1984 | Calzi | 204/409 |
| 4,505,784 | 3/1985 | Mund et al. | 204/1 T |
| 4,512,852 | 4/1985 | Tsuboshime et al. | 204/1 T |
| 4,757,022 | 7/1988 | Shutts et al. | 204/415 X |
| 4,863,841 | 12/1982 | Snow | 428/35 |

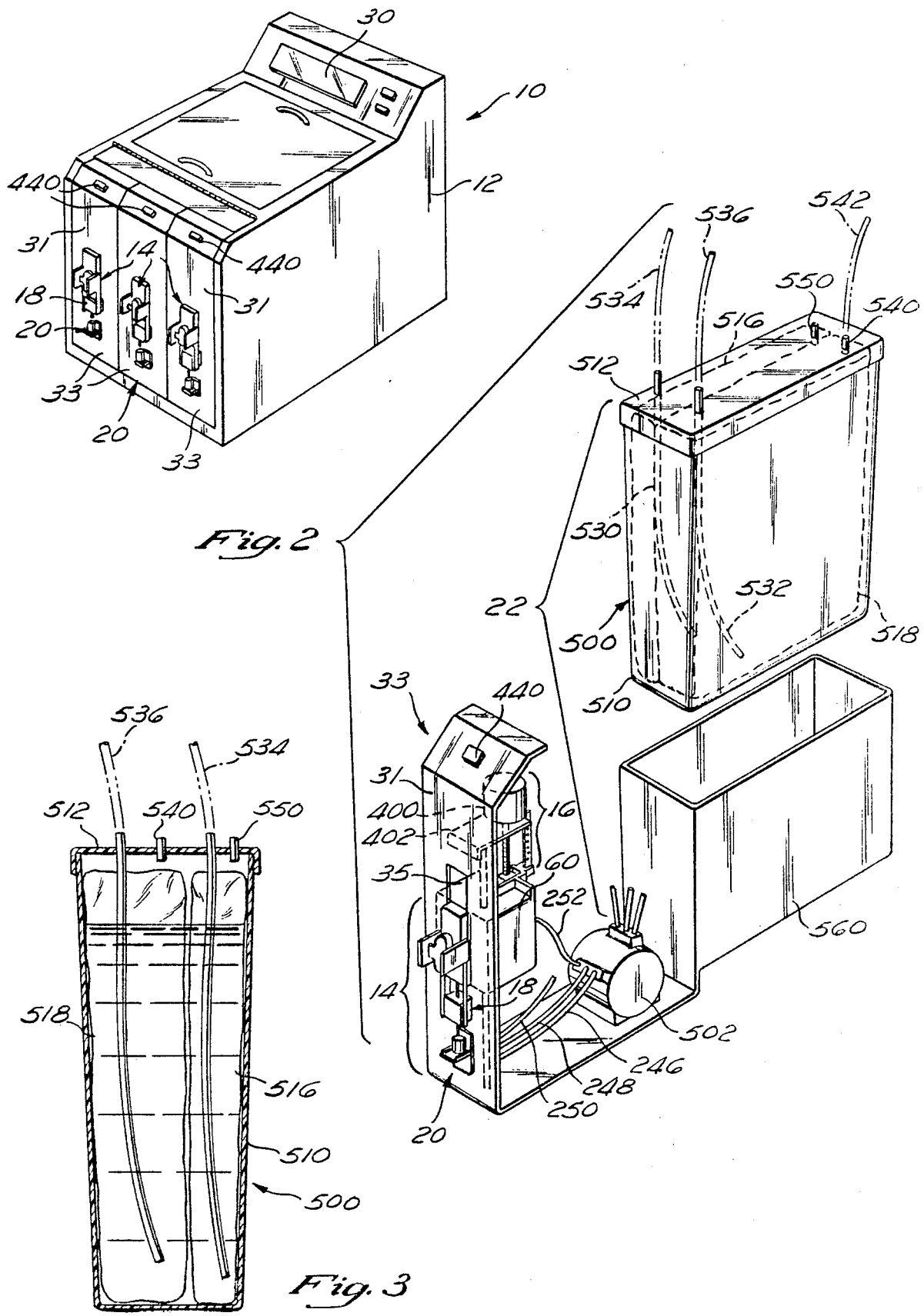

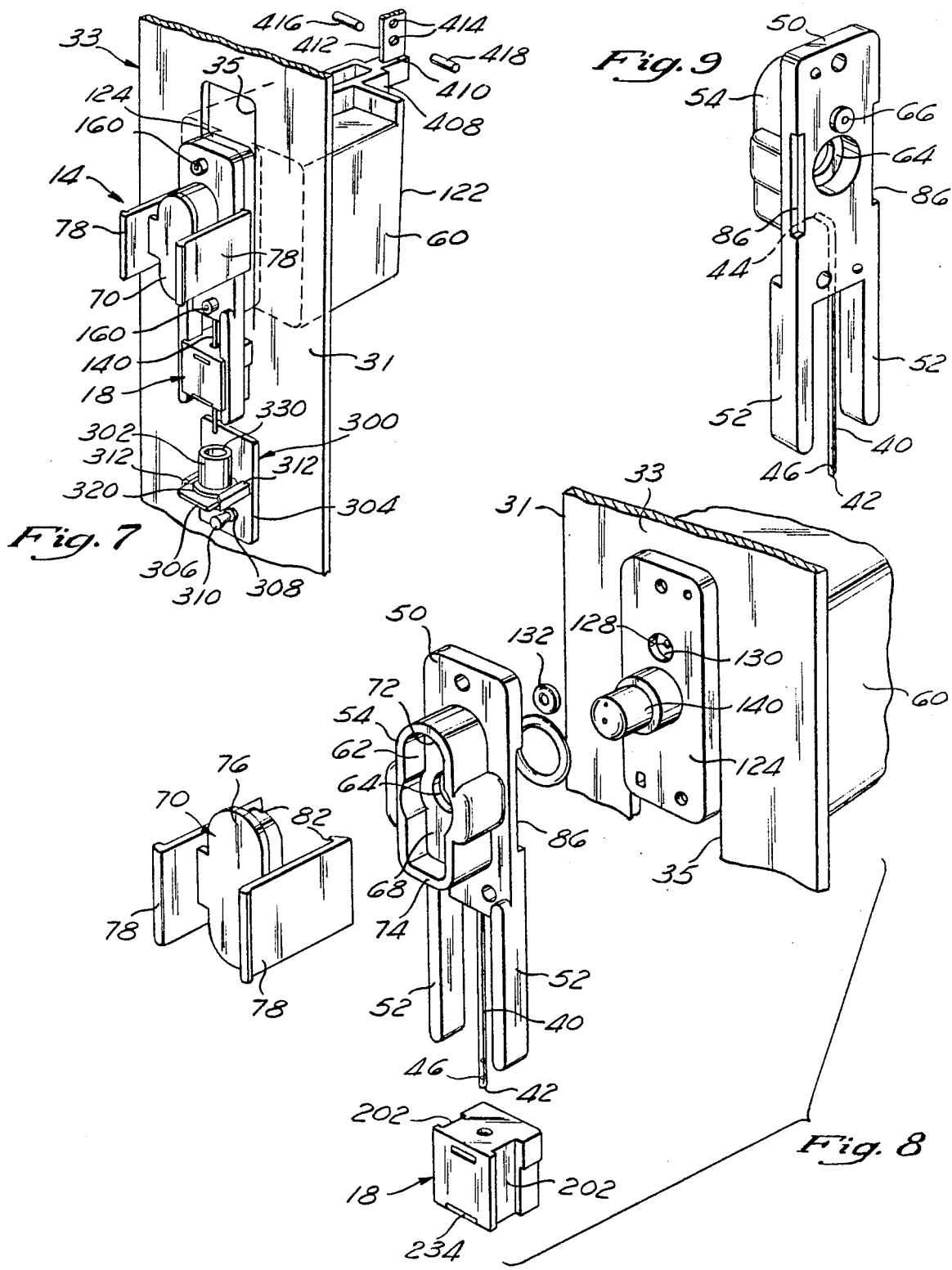

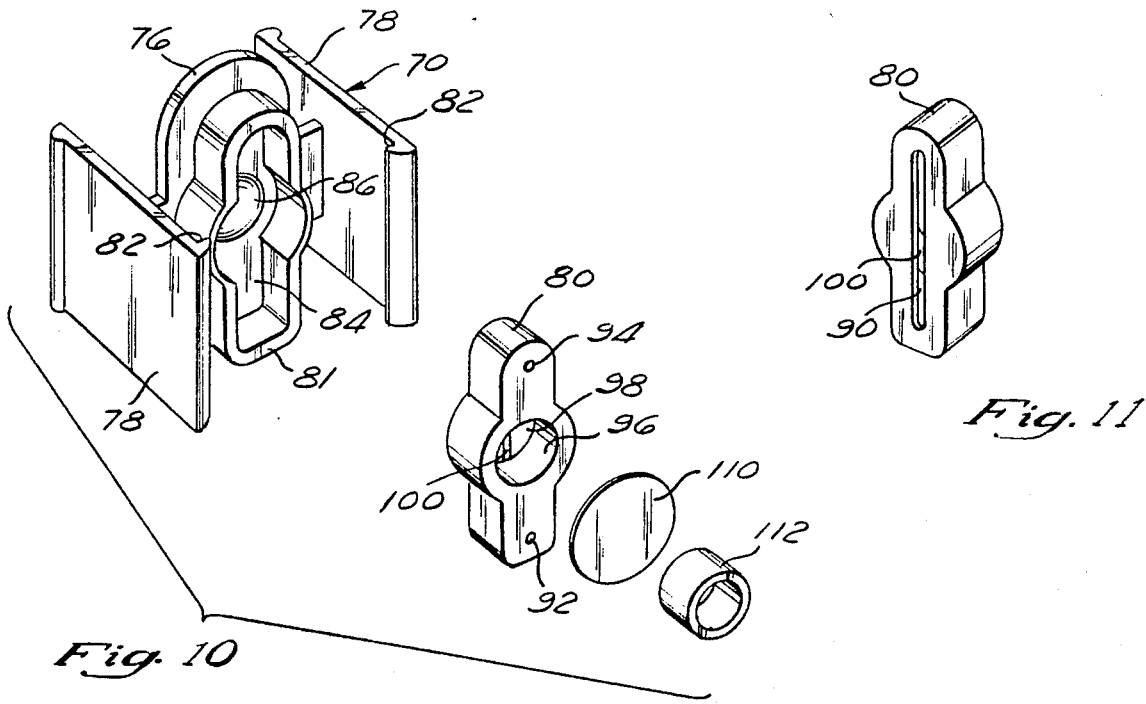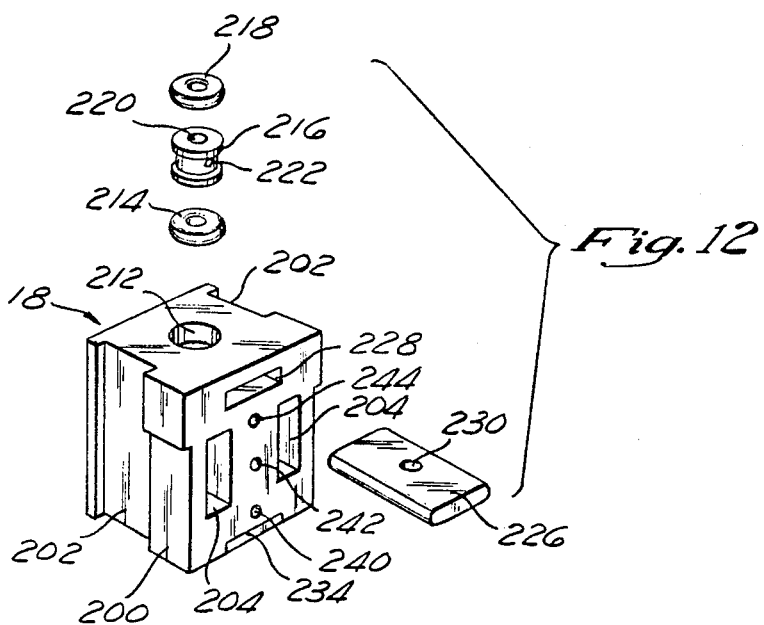

ing application Ser. No. 798,791 comprises an electrode

ENZYMATIC ELECTRODE AND ELECTRODE MODULE AND METHOD OF USE

This document includes a microfiche appendix with two fiches, containing 111 pages.

FIELD OF THE INVENTION

The present invention relates to enzymatic electrodes and, more particularly, to an enzymatic electrode and electrode module specifically adapted for use in a medical analyzer device which permits rapid analysis of substances of interest contained within an undiluted body fluid such as whole blood, serum and/or plasma. Pending U.S. patent application Ser. No. 798,791 filed Nov. 15, 1985 in the name of Max D. Liston, et al. entitled "Ion Selective/Enzymatic Electrode Medical Analyzer Device and Method of Use" and assigned to the assignee of the subject application discloses an automated modular multi-channel medical analyzer device characterized by use of an ion selective electrode and/or enzymatic electrode/wash cell system which permits analysis of substances of interest in body fluids. Although not limited in its application, the apparatus and method of the present invention, to be described hereinafter, is specifically adapted to be utilized in the medical analyzer structure disclosed in said 798,791 pending application and utilized as a substitute for the enzymatic electrode work station or analytical module disclosed therein.

Basically, the enzymatic electrode disclosed in pending application Ser. No. 798,791 comprises an electrode insert positioned upon the end of a probe which is selectively immersed in a body fluid sample. The insert includes a coaxially positioned sensor electrode and reference electrode located on one side of an enzyme bearing membrane. The membrane carries one or more enzymes for converting the substance desired to be measured by chemical reaction into a substance which is polarographically active. For example, the membrane may be provided with a glucose oxidase enzyme which converts glucose to gluconic acid and hydrogen peroxide with the hydrogen peroxide being detectable by polarographic techniques. In this regard, the hydrogen peroxide depolarizes the sensor electrode and current flow at a given applied voltage applied across the sensor electrode and reference electrode is proportional to the hydrogen peroxide concentration developed by the enzymatic chemical reaction adjacent the membrane. Thus, by measuring the current flow between the reference and sensor electrode and calibrating the same, a determination of glucose concentration or other substances of interest capable of being converted to a polarographically detectable substance through a membrane enzyme reaction may be obtained.

Although such enzymatic electrode disclosed in said pending 798,791 application comprises a significant improvement over the prior art, it has been found that the placement of the membrane on the distal end of an axially reciprocating probe runs the risk of causing inadvertent damage to the fragile membrane structure caused by either physical contact with support structures and/or resident time in an air environment as well as possible measurement delays or inaccuracies caused by the use of the rate and/or end point measurement system utilized for the enzymatic electrode. In this regard, the use of the rate and/or end point measurement method requires rather intricate software to recognize appropriate measurement points to derive a desired resultant measurement value.

SUMMARY OF THE PRESENT INVENTION

The present invention comprises an improved enzymatic electrode and electrode module specifically adapted for use in a medical analyzer device which permits rapid analysis of substances of interest contained within undiluted body fluids such as whole blood, serum and/or plasma. Although not limited in application, the improved enzymatic electrode and electrode module of the present invention is specifically adapted for use upon the medical analyzer device disclosed in pending U.S. patent application Ser. No. 798,791 and may be utilized as a substitute for the enzymatic electrode and analytical module disclosed therein. In this regard, the present invention takes a substantial departure from the teachings of the prior art in the following areas: (1) probe/electrode/membrane construction and support system; (2) membrane construction; (3) membrane chemistry and reagents; and (4) a pseudo-rate/created peak measurement technique. Although each of these departures has independent application in the art, the combination of the same in a composite enzymatic electrode system results in a synergistic combination rendering the present invention a significant improvement in the art.

The significant departure of the present invention in relation to the probe/electrode/membrane construction and support system comprises the enzymatic electrode continuously being in fluid communication with an axially reciprocating probe which selectively transports a quantity of separate and distinct solutions, i.e. a buffer aqueous solution, a calibrant aqueous solution and a body fluid sample to a membrane positioned adjacent the enzymatic electrode. The buffer aqueous solution and calibrant aqueous solution are presented at a wash cell while the body fluid sample desired to be analyzed is disposed in a sample cup positioned axially beneath the wash cell. The probe is axially driven to differing vertical locations within the wash cell and sample cup to selectively transport the aqueous solutions and body fluid sample to the membrane and subsequently into a waste reservoir. The enzymatic electrode comprises a series of three electrodes, i.e. a working or sensor electrode, a reference electrode, and a counter electrode, all of which are simultaneously disposed in the membrane solution flow path so as to be in fluid communication with the aqueous solutions and body fluid being analyzed. The counter electrode additionally is formed in a novel construction which permits the electrode to comprise an electrical electrode function as well as a mechanical fluid path function. The wash cell is so constructed to insure that residual fluid and air bubbles possibly accumulating on the probe during axial reciprocation are dislodged therefrom and segregated from the aqueous solutions and/or body fluid sample flow to the membrane. Further, the membrane is removably attached to the electrode and the aqueous solutions are housed and supported in novel manners which permit rapid replacement of the same by non-skilled personnel.

The membrane construction of the present invention comprises a composite multi-layer membrane composed of a protective membrane layer, an active enzyme membrane layer and limiting membrane layer. The protective enzyme layer comprises either a single or preferably multi-layered structure which is adapted to screen out, i.e. prevent the passage of blood cells and other large particulate or cellular structures therethrough. Further, the protective membrane layer is formed to adjust the transport rate of an analyte or substance desired to be measured into the enzyme layer which aids in the calibration and linearization of the electrical signal developed by the enzymatic electrode. In addition, the protective layer may include an immobilized enzyme such as catalase when glucose measurements are desired to be effectuated at the membrane, which insures that sufficient oxygen is present at the membrane such that high glucose concentrations will not drive the enzyme reaction beyond system parameters. The active enzyme layer comprises an immobilized enzyme which converts the substance desired to be measured into a detectable substance in the presence of the enzyme, i.e. preferably a polarographically detectable substance. The limiting membrane layer is formed to selectively screen out or deter the passage therethrough of interfering low molecular weight substances which could cause errors in measurement accuracy, yet permit the relatively free or unrestricted transport of the polarographically detectable substance to the electrode. In the preferred embodiment the membrane layer achieves this screening function by impeding the transport rate of interfering substances therethrough for a sufficient period of time to enable detection and measurement of the substance of interest at the electrode without interference. Thus, with the novel membrane construction of the present invention, the body fluid desired to be analyzed can be presented at the membrane in an undiluted condition with interfering substances being inhibited or impeded from interaction with the electrode and the desired substance of interest to be measured being rapidly converted into a polargraphically detectable substance.

Pertaining to membrane chemistry and reagents, the present invention specifically defines the chemistry and drives the natural kinetics of the enzyme reaction to optimize measurement performance and accuracies. More particularly, by use of the protective membrane, the present invention contemplates controlling the rate at which the substance of interest desired to be measured enters into the active enzyme layer of the membrane to thereby insure the linearization of the electrical signal measured at the electrode (i.e. the electrical signal measured at the electrode is linearly proportional to the concentration of the substance desired to be measured in the body fluid sample). Further, by use of immobilized catalase in the protective layer which for purposes of glucose measurement converts hydrogen peroxide to oxygen and water, sufficient oxygen is presented at the membrane to insure that high glucose concentrations will not drive the enzyme reaction beyond system parameters.

In addition, the resident time which the calibrant aqueous solution and/or body fluid sample is exposed to the membrane is carefully controlled by selective introduction of the buffer aqueous solution so as to cause at desired time periods, a reverse diffusion of the substance desired to be measured across the membrane. This reverse diffusion thereby creates an easily recognized artifically created peak value measurement signal which, as will be explained in more detail infra, significantly reduces exposure time and maximizes signal performance considerations.

In contrast to the prior art rate or end point measuring techniques of an enzymatic electrode, the present invention incorporates a novel pseudo-rate/created peak measurement technique which enables a desired peak value of the signal generated at the electrode to be rapidly identified. Further, in view of the rapid identification of the peak signal value, data storage and processing are maintained at a minimum, thereby simplifying the measurement process.

DESCRIPTION OF THE DRAWINGS

These as well as other features of the present invention will become more apparent upon reference to the drawings wherein:

FIG. 1 is a perspective view showing a medical analyzer device having multiple enzymatic analytical modules or test stations of the present invention inserted and housed therein;

FIG. 2 is an exploded perspective view depicting an analytical module removed from the analyzer of FIG. 1 and illustrating an aqueous storage/waste reservoir positionable therein;

FIG. 3 is a cross-sectional view of the aqueous storage/waste reservoir shown in FIG. 2;

FIG. 7 is an enlarged perspective view of the electrode carriage mounted to the probe and membrane chamber and illustrating the orientation of the same relative to the wash cell and sample cup;

FIG. 8 is an exploded perspective view illustrating the interrelationship between the membrane chamber, probe and electrode carriage;

FIG. 10 is an exploded perspective view of the membrane holder, membrane gasket, membrane and membrane retainer ring of the present invention;

FIG. 11 is an enlarged perspective view of the membrane gasket of the present invention;

FIG. 12 is an exploded perspective view of the wash cell of the present invention;

DETAILED DESCRIPTION OF THE PREFERRED EMBODIMENT

Figure 4:
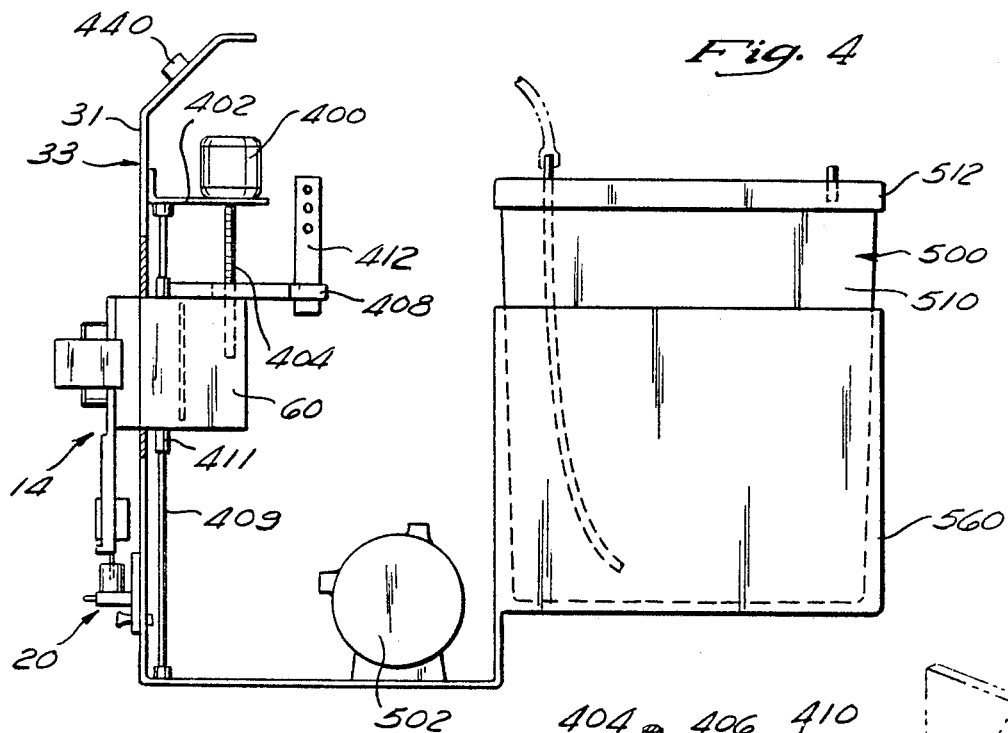
FIG. 4 is an elevational view of the enzymatic analytical module or work station of the present invention.
Figure 5:
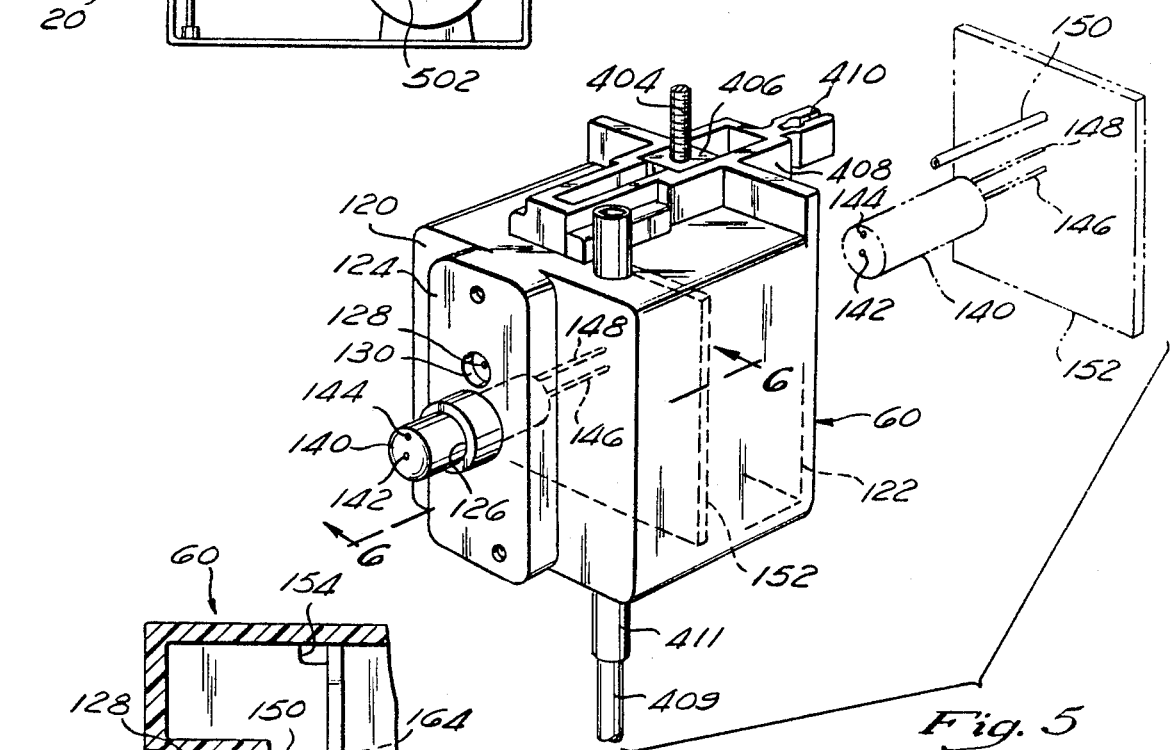
FIG. 5 is an exploded perspective view of the electrode carriage of the present invention.

Referring to FIG. 1, there is shown a medical analyzer device 10 composed generally of a housing 12 which supports or slidably receives one or more enzymatic test stations or analytical modules 33 of the present invention. As best shown in FIG. 2, each of the analytical modules 33 carry the major subassemblies and subcomponents for the analyzer 10, namely a probe/membrane/electrode assembly 14, a probe drive mechanism 16, a wash cell assembly 18, a sample cup/holder assembly 20 and a fluidic pump and vacuum system 22. The operation of each of the modules 33 and thus their respective subassemblies 14, 16, 18, 20 and 22 are controlled by common processing and control electronics (not shown) which are carried upon a main circuit board (not shown) disposed adjacent the rear of the housing 12. Each of the modules 33 are electrically connected via conventional pin connectors (not shown) and multiplexed to the common processing and control electronics such that the selective operation of all of the modules 33 can be advantageously facilitated by use of a single microprocessor.

The description of the common processing and control electronics, main circuit board and the electrical connection of the same to each of the modules 33 is thoroughly disclosed in pending U.S. patent application Ser. No. 798,791 filed Nov. 15, 1985 in the name of Max D. Liston et al., entitled "Ion Selective/Enzymatic Electrode Medical Analyzer Device and Method of Use" and assigned to the assignee of the subject application, the disclosure of which is expressly incorporated herein by reference. Although not limited in its application, the enzymatic electrode module 33 of the present invention and its method of use is specifically adapted to be utilized in the medical analyzer structure disclosed in said 798,791 pending patent application and is utilized as a substitute for the enzymatic electrode work station or analytical module disclosed therein.

As will become more apparent infra, the interaction of the various subassemblies 14, 16, 18, 20 and 22 of the module 33 with the processing and control electronics provides an accurate determination of the concentration of substances of interest such as glucose, creatinine, triglyceride, cholesterol, ascorbic acid, amino acid, lactose, galactose and other substances contained within an undiluted body fluid sample such as whole blood, serum or plasma. As will be recognized, all of these substances of interest comprise substances which in the presence of a suitable enzyme, may be converted to a detectable substance and measured by various sensor techniques.

As a basic overview, analysis of the body fluid specimen for a particular substance of interest is accomplished by the probe/membrane/electrode assembly 14 of a module 33 being axially reciprocated by the probe drive mechanism 16 between the wash cell assembly 18 and the sample cup/holder assembly 20. At selected axial positions of the probe/membrane/electrode assembly 14 within the wash cell assembly 18 and sample cup/holder assembly 20, the fluidic pump and vacuum system 22 serves to selectively draw either a buffer aqueous solution and/or calibrant aqueous solution presented at the wash cell 18 or the body fluid sample 20 contained within the sample cup/holder assembly 20, upwardly into the probe/membrane/electrode assembly 14 to present the same at a membrane positioned adjacent the enzymatic electrode. The calibrant aqueous solution and body fluid sample or specimen, upon contact with the membrane, are converted via an enzyme reaction. A product of this reaction passes through the membrane to a specific product sensitive sensor preferably but not limited to an electrode to generate a detectable signal preferably an amperometric detectable electrical signal. By processing the electrical signal in conformity with system parameters, a resultant determination of the concentration of the particular substance of interest desired to be measured within the body fluid specimen is rapidly achieved and presented upon the display panel 30 of the analyzer 10.

With this operational overview, a detailed description of the construction of each of the major subassemblies and subcomponents of the present invention is provided.

PROBE/MEMBRANE/ELECTRODE ASSEMBLY

Referring generally to FIGS. 3 through 10, the probe/membrane/electrode assembly designated generally by the numeral 14 is depicted. As shown, the assembly 14 is disposed adjacent the outer surface of the front panel 31 of the analytical module 33 and is composed generally of a membrane and probe carriage or housing 50, electrode carriage 60 and membrane holder 70. As best shown in FIGS. 8 and 9, the membrane and probe carriage 50 comprises an elongate structure having a pair of guide rails 52 extending vertically downward at its lowermost end and a membrane chamber 54 extending laterally outward from its frontal surface. A tubular probe 40 preferably formed of stainless steel and having an approximate length of two inches, an outside diameter of 0.062 inches and an inside diameter of 0.050 inches is formed as an insert and rigidly retained upon the carriage 50. The probe 40 has a closed lower end 42 and an open upper end 44 which is oriented horizontally outward and extends into the interior of membrane chamber 54. A small radially extending aperture 46 is provided in the probe 40 adjacent its lower closed end 42 which as will be explained in more detail infra, serves as a fluid inlet for the probe 40.

The membrane chamber 54 which is preferably formed as an integral portion of the carriage 50 defines an interior region 62 having an enlarged central aperture 64 and smaller upper aperture 66 extending horizontally therethrough. The interior region 62 of the membrane chamber 54 is formed to have a flat planar rear surface 68 as well as dissimilarly shaped end portions 72 and 74 which form a keying function to prevent the improper mounting of the membrane gasket 80 and membrane holder 70 thereon.

Referring more particularly to FIGS. 8, 10 and 11, the membrane holder 70 includes a central cover portion 76 and a pair of elongate wings or tabs 78 positioned on opposite sides thereof. The central portion 76 includes a horizontally extending flange 81, the exterior configuration of which is formed in a complimentary configuration to the interior region 62 of the membrane chamber 50 such that the flange may extend therein. The tabs 78 include a pair of retaining shoulders 82 at their distal end thereof which are sized to extend over and be received within a pair of recesses 86 formed on edges of the rear surface of the membrane/probe carriage 50. As will be recognized, the location of the shoulders 82 is positioned to provide a slight compression fit of the central portion 70 of the membrane holder against the membrane chamber 54 when the shoulders 82 are captured in the recesses 86. Further the tabs 78 are formed to laterally spread when a manual compression force is applied to their outermost distal ends to allow the shoulders 82 to extend into the recesses 86 and upon release of the manual compression force, biasingly return to their initial configuration to tightly maintain the membrane holder 70 upon the carriage 50.

The interior of the flange 81 defines a rear planar surface 84 having a concave recess 86 formed centrally therein. The interior of the flange 81 receives a membrane gasket 80, preferably fabricated of a resilient latex, silicon rubber or elastomeric material which is formed having an exterior configuration complimentary to the configuration of the interior of the flange 81 so as to be tightly received therein. The outer surface of the gasket 80 includes a vertically extending recess 90 which communicates at opposite ends thereof with a pair of annular apertures 92 and 94 extending laterally through the gasket 80. The gasket 80 is additionally provided with an enlarged central annular cavity 96, the interior face of which 98 is formed in a concave configuration complimentary to the concave configuration of the recess 86 formed in the membrane holder 70. As best shown in FIG. 11, the recess 90 extends through the concave face 98 of the cavity 96 forming an opening 100 through the gasket 80.

The cavity 96 of the gasket 80 is sized to receive a thin composite membrane 110 which is preferably formed to have a diameter greater than the diameter of the cavity 96. The membrane 110 is inserted within the interior of the cavity 96 by way of a retainer ring 112 which is formed having an outside diameter slightly greater than the diameter of the cavity 96. As such, by centering the retainer ring 112 relative the composite membrane 110 and subsequently pressing the membrane 110 and retainer ring 112 axially within the interior of the cavity 96, the membrane 110 is positioned adjacent the concave face 98 of the gasket 80 and is disposed within the opening 100 of the recess 90. In the preferred embodiment, the width of the gasket 80 is sized to be slightly greater than the depth of the interior of the annular flange 81 such that when the gasket 80 is positioned within the membrane holder 70 and the membrane holder 70 is assembled to the membrane chamber 54 by way of the tabs 78, the gasket forms a fluid tight flow path defined by the recess 90 extending between the upper open end 44 of the probe 40 and annular aperture 66 of the membrane probe carriage 50.

Referring more particularly to FIGS. 5 through 8, the electrode carriage 60 is formed in a generally rectangular or box-like configuration having a frontal surface 120, and open rear end 122. A rectangular shaped laterally extending boss 124 is presented at the frontal surface 120 which includes an enlarged central aperture 126 extending partially therethrough, and a smaller aperture 128 extending completely therethrough. The aperture 128 includes a annular recess 130 at its frontal end which is sized to receive an O-ring 132 (shown in FIG. 8). The central aperture 126 is sized to tightly receive an electrode or sensor insert 140 which comprises a cylindrical member formed of an electrically insulating material.

Figure 6:
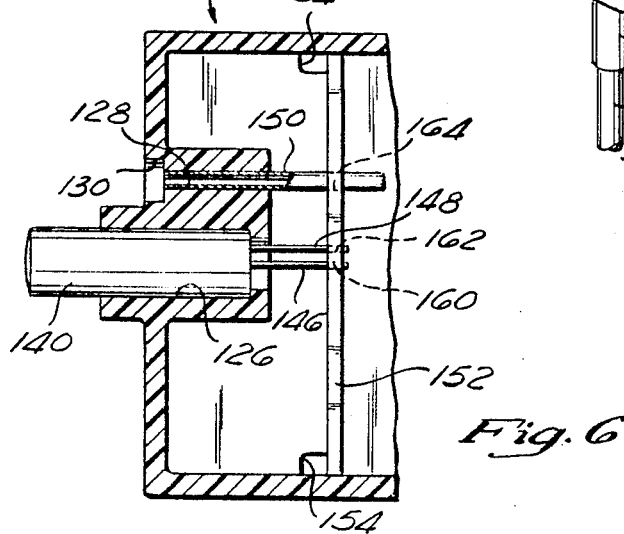
FIG. 6 is a cross-sectional view taken about lines 6—6 of FIG. 5.

The electrode insert includes a working or sensor electrode 142 and reference electrode 144 extending axially therethrough having their outermost surface disposed on the convex shaped outer face of the electrode member and their inner ends connected to respective pin terminals 146 and 148. In the preferred embodiment the working or sensor electrode 142 comprises a platinum wire having a diameter of approximately 0.040 inches which preferably has a coined or enlarged head having a distal diameter of approximately 0.080 of an inch, while the reference electrode comprises a silver wire having a diameter of approximately 0.020 inches. The electrode carriage 60 additionally includes a counter electrode 150 press fit within the aperture 128 formed therein. As best shown in FIG. 6, the counter electrode 150 is perferably formed as a hollow stainless steel tube which extends from the O-ring recess 130 and rearwardly outward toward the open end 122 of the carriage 60. A printed circuit board 152 is disposed within the interior of the carriage 60 and is located by a pair of mounting shoulders 154 so as to be rigidly affixed therein. The printed circuit board 152 includes conventional electrode amplifier circuitry and forms an electrical interface between the electrodes 142, 144 and 150. This interface is accomplished by the circuit board 152 including three through-hole plated apertures 160, 162, and 164 (shown in FIG. 6) which frictionally engage or receive the pin terminals 146, 148 and outside diameter of the counter electrode 150 respectively. As such, it will be recognized that when necessitated, all electrodes 142, 144 and 150 of the present invention may be rapidly replaced merely by removal and insertion of duplicate electrodes into the apertures 126 and 128 and into the through-hole plated circuit board 152.

The probe/membrane/electrode assembly 14 is assembled upon the analytical module 33 by positioning the electrode carriage 60 on the interior side of the front surface 31 of the module 33 and extending the boss 124 of the electrode carriage 60 through an elongate rectangular aperture 35 (best shown in FIG. 2) formed in the front surface 31 of the module 33. The membrane and probe carriage 50 may then be inserted from the front side of the frontal panel 31 toward the boss 124 causing the outboard end of the electrode insert 140 to extend within the enlarged central aperture 64 of the membrane chamber 54. Continued inward movement of the membrane/probe carriage 50 toward the electrode carriage 60 causes the rear surface of the membrane/probe carriage 50 to abut the frontal surface of the boss 124. Upon this abutment, the O-ring 132 is compressed within the recess 130 forming a fluid-tight interface between the aperture 66 formed in the membrane probe carriage 50 and the tubular counter electrode 150. Subsequently, the membrane/probe carriage 50 and electrode carriage 60 may be maintained in their proper assembled orientation by way of machine screws 160 (shown in FIG. 7) which are threadingly inserted through aligned apertures formed in the membrane and probe carriage 50 and raised boss 124 of the electrode carriage 60.

The membrane gasket 80 having the membrane 110 disposed therein may then be inserted into the membrane holder 70 and the membrane holder 70 may be aligned with the membrane chamber 54. By applying a minor compression force to the distal ends of the tabs 78 of the holder 70, the holder 70 may then be pushed inwardly causing the membrane gasket to form a fluid-tight seal against the planar face 68 of the membrane chamber 54. Upon releasing the compression force to the tab 78, the seal of the gasket against the planar face 68 is maintained due to the interaction of the shoulders 82 of the membrane holder 70 with the recesses 86 formed on the rear edges of the membrane/probe carriage 50.

Figure 13:
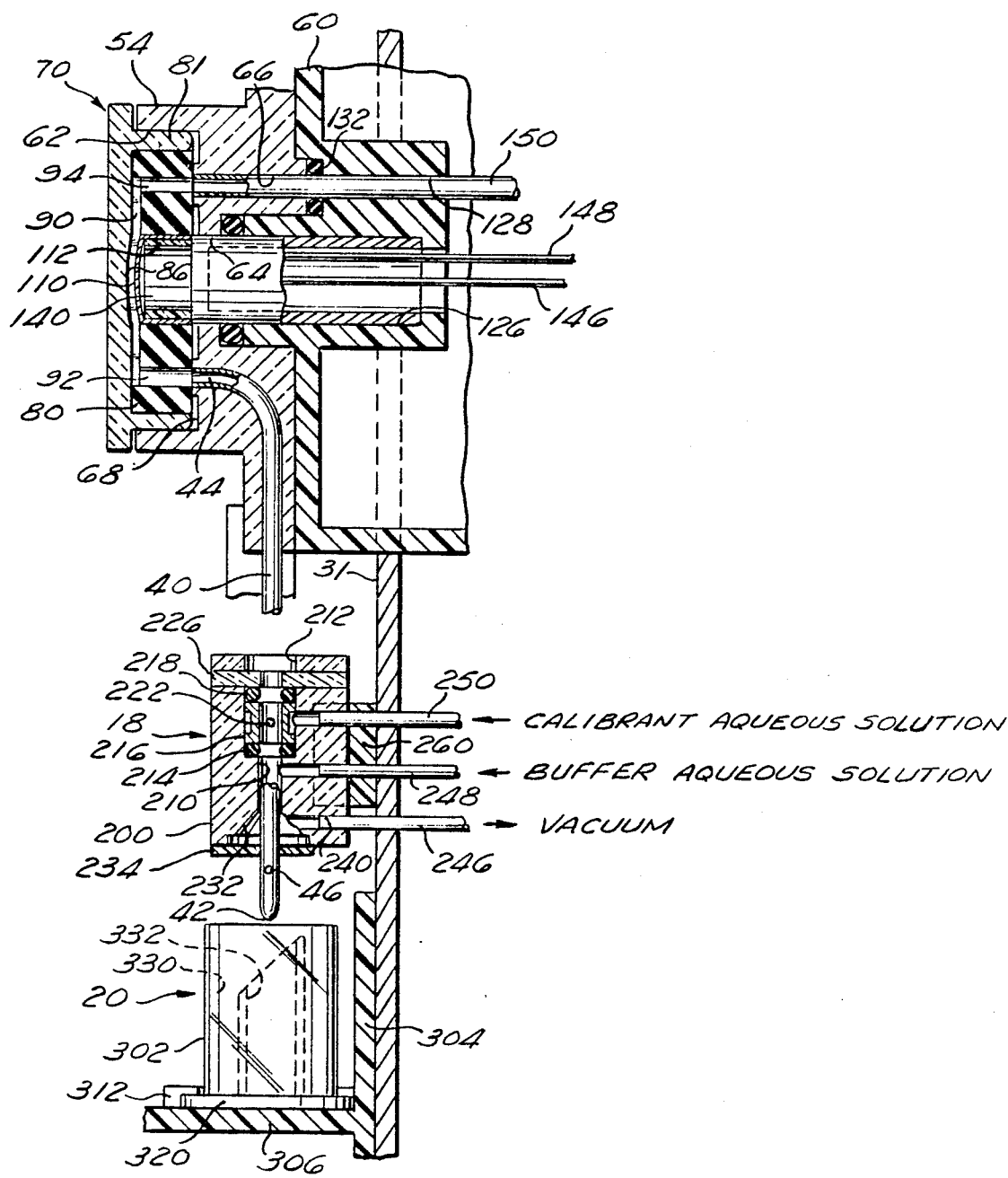
FIG. 13 is a partial cross-sectional view of the electrode carriage, membrane chamber, membrane holder, probe and wash cell of the present invention illustrating their relative orientation and depicting the internal flow channels formed therein and flow conduits attached thereto

As best shown in FIG. 13, by this particular assembly, the convex end of the electrode insert 140 directly abuts the inboard surface of the composite membrane 110 and thereby causes the membrane 110 to be pushed tightly against the face of the electrode insert 140 and inwardly toward the concave recess 86 formed in the membrane holder 70 such that the membrane 110 is maintained in moderate tension and the distal ends of the sensor 142 and reference 144 electrodes contact the membrane 110. As such, mounting and replacement of the membrane 110 can be effectuated rapidly and conveniently by unskilled personnel without disturbing the mounting of the electrodes within the membrane chamber merely by manipulation of the membrane holder 70.

Further, an internal flow path is defined from the inlet aperture 46 of the probe 40 through the interior of the probe 40 through the aperture 92, recess 90 and aperture 94 of the membrane gasket and through the interior of the counter electrode 150. As will be recognized, this flow path insures that all fluid flow is presented at the exterior surface of the membrane 110 and further, that all electrodes 142, 144 and 150 are disposed within the fluid path with the counter electrode 150 being directly exposed therein, while the working and reference electrodes 142 and 144 being disposed therein via their interaction with the composite membrane 110.

WASH CELL ASSEMBLY

Referring more particularly to FIGS. 12 and 13, the wash cell assembly designated generally by the numeral 18 is depicted. As shown, the wash cell 18 comprises a generally rectangular shaped housing or vessel having a pair of flats 202 formed along its side edges which are sized to slidingly receive and thereby be aligned with the downwardly extending guide rails 52 of the membrane probe carriage 50. A pair of rectangular mounting apertures 204 are provided along the rear surface of the wash cell housing 200 and extend laterally therein. A central aperture 210 extends vertically through the entire length of the housing 200 (best shown in FIG. 13), the diameter of which is slightly larger than the diameter of the probe 40 such that the probe may be reciprocated axially therethrough. The upper portion of the central aperture 210 includes an enlarged diameter bore 212 which receives an O-ring 214, spacer spool 216 and an additional O-ring 218 therein. The spacer spool 216 includes an axial aperture 220 extending therethrough which is additionally sized to have a diameter slightly greater than the diameter of the probe 40 and additionally includes a radially extending aperture 222 which extends through the central reduced diameter section of the spool 216 and into the axial aperture 220. The O-rings 214 and 216 are formed to have an interior diameter slightly less than the outside diameter of the probe 40 such that the O-rings form a dynamic fluid seal thereabout when the probe reciprocates axially through the wash cell 18.

The O-ring 214, spacer spool 216 and O-ring 218 are inserted within the enlarged bore 212 and are retained therein by way of a retainer plate 226 which is slidingly received within a complimentarily shaped, laterally extending aperture 228 formed adjacent the upper surface of the housing 200. As will be recognized, when the retaining plate is inserted within the aperture 228, it axially compresses the O-rings 214 and 218 against the spacer spool 216 and against the cylindrical wall of the enlarged bore 212. The retainer plate 226 additionally is provided with a central aperture 230 sized to have a diameter slightly greater than the diameter of the probe 40 and positioned so as to be in axial alignment with the central aperture 210 extending through the wash cell housing 200. Three axially aligned and vertically spaced apertures 240, 242 and 244 extend laterally inward from the rear surface of the wash cell housing 200 and into the central aperture 210 which receive at the inboard end a respective fluid conduit 246, 248 and 250. The lowermost end of the central aperture 210 at the region adjacent the inner section of the aperture 240 additionally includes a frustro-conical shaped aperture 232 which as will be explained in more detail infra, is specifically designed to dislodge or strip any residual sample and air bubbles accumulating on the probe 40 during reciprocation of the probe 40 through the wash cell 18. A lower cover plate 234 having a central aperture formed therein is rigidly affixed to the lower end of the housin 200 thereby covering the frustro-conical shaped aperture 232.

By this construction of the wash cell 18, three separate vertically segregated zones or regions are provided along the length of the central aperture 210 with the lowermost region being defined by the aperture 240 and frustro-conical shaped aperture 232, the second or middle region being defined by the central aperture 210 and aperture 242 and the third or upper region being defined by the reduced diameter portion of the spacer spool 216 and aperture 244. As will be explained in more detail infra, these segregated regions or zones of the wash cell 18 are utilized to permit the selective and separate flow of a buffer aqueous solution and calibrant aqueous solution upwardly within the interior of the probe 40 and to the membrane 110 as well as cleaning of the probe 40 prior to movement of the probe between the separate regions.

As best shown in FIG. 13, the wash cell is assembled to the analytical module 33 adjacent the front surface 31 and is disposed vertically below the probe/membrane/electrode assembly 14. In this regard, the wash cell 18 is mounted to the module 33 by interaction of the rectangular mounting apertures 204 upon a pair of mounting tabs 260 (shown in FIG. 13) which extend laterally outward from the front surface 31 of the module 33. With the mounting tabs 260 inserted within the mounting apertures 204 and the guide rails 52 of the membrane and probe carriage 50 being inserted into the flats 202 of the wash cell, the central aperture 210 of the wash cell 18 is coaxially aligned with the probe 40 of the probe/membrane/electrode assembly 14.

SAMPLE CUP/HOLDER ASSEMBLY

The sample cup/holder assembly is best illustrated in FIG. 7 and comprises a support shelf member 300 and specimen cup 302, all of which are preferably formed of a plastic material such as clear ABS. The support shelf member 300 is formed having a generally rectangular shaped base member 304 and an integrally formed shelf plate 306 which extends perpendicularly therefrom. A mounting aperture 308 is provided in the lower portion of the base member 304 which receives a fastener 310 extending through the front surface 31 of the analytical module 33 to rigidly attach the base member 304 to the module 33. The shelf member 306 is provided with a pair of L-shaped channels 312 which extend vertically upward from the shelf member 306 and are sized to slidingly receive a portion of the specimen cup 302. The sample cup 302 possesses a generally barrel-like configuration having an enlarged cylindrical base portion 320, the diameter of which is equal to or slightly smaller than the spacing between the L-shaped channels 312. As best shown in FIG. 13, a central aperture 330 extends axially downward within the interior of the sample cup 302. A smaller diameter cylinder 332 (indicated by the phantom lines in FIG. 13) is coaxially positioned within the interior of the aperture 330 and is sized having a diameter slightly greater than the diameter of the probe 40. The upper end of the aperture 332 terminates axially below the upper end of the aperture 330 and includes an angularly inclined surface. The depth of the aperture 332 is preferably sized to hold a relatively small quantity of body fluid (approximately 40 to 125 microliters and preferably 75-100 microliters). As will be recognized, with the support shelf 300 rigidly attached to the frontal surface 31 of the analytical module 33 and the sample cup 302 slidably received within the L-shaped channels 312, the axis of the aperture 332 is aligned with the axis of the probe 40 such that the probe may be reciprocated downwardly within the interior of the aperture 332.

PROBE DRIVE MECHANISM

The probe drive mechanism designated generally by the numeral 16 axially reciprocates, i.e. transports the probe/membrane/electrode assembly 14 such that the lower end of the probe 40 is selectively and intermittantly disposed in the sample cup 302 and within the axially segregated regions of the wash cell 18. As best shown in FIGS. 2 and 4, the probe drive mechanism 16 includes a linear actuator or step motor 400 which is mounted upon a support shelf 402 extending inwardly from the upper interior of the front surface 31 of the analytical module 33. The actuator or motor 400 serves to selectively drive or rotate a lead screw 404 in both a clockwise and counter-clockwise direction. The lead screw engages a complimentary threaded connection block 406 which is slidingly received in a laterally extending mounting track 408 formed adjacent the uppermost surface of the electrode carriage 60. During rotation or movement of the lead screw 404 by the motor 400, the electrode carriage 60 is vertically reciprocated either toward or away from the mounting plate 402 with such reciprocal travel being guided by a vertically extending guide pin 410 rigidly mounted to the module 33 and extending through a guide bushing 412 mounted to the electrode carriage 60. In the presently preferred embodiment, the step motor 321 is implemented as a model LP221-P2 four phase step motor manufactured by Airpax, a Division of North American Phillips Corporation, however, other suitable analogous or related implementation is contemplated herein.

The inward distal end of the mounting track 408 is provided with a rectangular slot 410 which mounts a rectangular flag member 412 extending vertically upward from the electrode carriage 60. The flag 412 is provided with one or more apertures 414, the vertical spacing of which is commensurate with the vertical spacing between the sample cup 302 and plural axial segregated regions within the wash cell 18. One or more conventional optical sensors (illustrated schematically in FIG. 7) are mounted to the analytical module 33 adjacent the support shelf 402 comprising an optical transmitter 416, and optical receiver 418 disposed on opposite sides of the flag 412. As is well known, when the optical receiver 418 receives the optical beam emanating from the optical transmitter 416, (as when the beam is aligned with one of the apertures 414 on the flag 412) an electrical output signal is generated which is indicative of the axial position of the probe/membrane/electrode assembly 14.

FLUIDIC PUMP AND VACUUM SYSTEM

The fluidic pump and vacuum system (designed generally by the numeral 22) is best depicted in FIGS. 2, 4 and 13 and is composed generally of a solution storage/waste reservoir 500, pump 502, plural flexible conduits 246, 248, and 252 which extend from the pump 502 to the apertures 240 and 242 of the wash cell 18 and the distal end of the counter electrode 150 respectively; and flexible conduit 250 which extends from the aperture 244 of the wash cell 18 directly to reservoir 500. The pump 502 illustrated schematically in the Figures may advantageously comprise a multiple channel (preferably a four channel) peristaltic pump unit which is adapted to provide vacuum or suction through the conduits 246 and 252 while providing a positive fluid displacement through the conduit 250; however, substitute analogous pumps and/or pumping systems may additionally be utilized.

Preferably, the solution storage/waste reservoir 500 comprises a disposable sealed unit having a base housing portion 510 and cover housing portion 512. Disposed within the interior of the reservoir 500 are a pair of flexible bag reservoirs 516 and 518 (illustrated by phantom lines in FIG. 2) which are positioned in a side-by-side orientation and carried within the interior of the housing portions 510 and 512. The flexible bag reservoir 516 is filled with a stablized aqueous calibrant solution containing a known concentration of the desired substance to be measured by the electrode upon the analytical module 33 while the other flexible bag reservoir 518 is filled with a similar aqueous solution having a different known concentration or no amount of the desired substance of interest to be measured upon the module. Further, this solution, i.e. buffer aqueous solution may contain one or more buffers and/or stabilizers such as a phosphate buffer and a sodium azide stabilizer. Since as will be explained in more detail infra, the operation of the present invention utilizes a substantially greater quantity of the buffer aqueous solution as opposed to the calibrant reagent solution, the size of the flexible bag reservoir 518 is normally substantially greater than the size of the reservoir 516.

A pair of induction conduits 530 and 532 are provided within the interior of the flexible bag reservoirs 516 and 518 respectively and extend upwardly through the cover portion 512 of the storage/waste reservoir 500. Flexible conduits 534 and 536 are attached to the upper end of the conduits 530 and 532 respectively. The conduit 536 extends to intake ports of the pump 502 such that the buffer aqueous solution may be supplied by the pump 502 to the wash cell 18 via conduit 248. The conduit 534 extends directly to the conduit 250 of the wash cell 18 to present calibrant solution to aperture 244 of the wash cell. The cover portion 512 of the reservoir 500 additionally is provided with an inlet port 540 which extends within the interior of the reservoir 500. A suitable, flexible conduit 542 may be attached at one end to the inlet port 540 and extend to the pump 502 to form a common discharge line for two channels of the pump 502 applying vacuum through the conduit 246 extending to the wash cell 18 and conduit 252 extending to the counter electrode 150. The cover portion 512 of the reservoir 500 may additionally include a vent port 550 which allows the escape of air contained within the interior of the reservoir 500 yet prevents any leakage of waste reagent solution from the reservoir 500.

As will be recognized, upon selective activation of the pump 502, vacuum is drawn through the lowermost aperture 240 of the wash cell 18 and the distal end of the counter electrode 150 while buffer aqueous solution is supplied to the middle aperture 242 of the wash cell 18. Further, calibrant solution is continuously presented without pumping to the upper aperture 244 of the wash cell 18. The selective operation of the pump 502 is controlled by the processing and control electronics of the analyzer 10 and pump operation is only initiated when the probe is stationary, i.e. when the inlet aperture 46 of the probe is disposed either in the sample cup 302 or within one of the segregated regions adjacent the apertures 240, 242 and 244 of the wash cell 18. As such, depending upon the axial position of the probe or, more particularly, the inlet aperture 46 thereof, activation of the pump 502 will cause either a body fluid sample contained within the sample cup 302, buffer aqueous solution presented at the central portion of the wash cell 18 or calibrant aqueous solution presented at the upper portion of the wash cell 18 to be drawn within the interior of the probe 40 across the membrane 110 through the counter electrode 150 and subsequently returned through the inlet port 540 into the interior of the reservoir 500. As will be recognized, in view of the fluidic pump and vacuum system of the present invention being a closed system, as calibrant and buffer aqueous solution is drawn from the flexible bag reservoirs 516 and 518 respectively, the spent solution is being returned through the inlet port 540 into the interior of the reservoir 500.

As best shown in FIG. 2, the entire solution storage/waste reservoir 500 is preferably sized to be received within a complimentary shaped sleeve 560 formed on the rear portion of the work station or analytical module 33 and may be rapidly removed therefrom to be disposed of in a biological, sanitary waste disposal system when required and further, may be rapidly replaced in an analogous manner.

COMPOSITE MEMBRANE

Although conventional prior art enzyme bearing membranes may be utilized in the subject application, in the preferred embodiment the present invention incorporates a novel composite membrane structure having a protective membrane layer adapted to prevent the passage of blood cells, particulates and cellular substances therethrough as well as adjust the diffusion rate of the analyte or substance of interest desired to be measured into the membrane; an active enzyme layer adapted to convert the desired substance of interest to be measured into a detectable substance, i.e. preferably polargraphically detectable substance; and a limiting membrane formed to inhibit or deter the passage of interfering low molecular weight substances therethrough and to the sensor or electrode. Those skilled in the art will recognize that although in the preferred embodiment an electrode is utilized as a sensing member for the membrane, other sensors such as thermistors, infra red sensors, photo sensors and the like are contemplated herein. Further, although in the prefered embodiment the substance desired to be measured is converted via an enzyme reaction into a polarographic detectable or amperometric detectable substance, other detectable substances are contemplated herein and for purposes of this application these terms shall be defined to include their broader definitions. Further, as will be recognized, depending upon the particular desired substance to be measured, the active enzyme layer membrane will be modified to include an appropriate enzyme which converts the desired substance to be measured into a suitably detectable substance. For purposes of discussion only and not by way of limitation, the construction of the composite membrane 110 of the present invention will be described in relation to an active enzyme layer utilized to measure glucose in blood. However, other enzymes for measuring other polargraphically detectable substances are contemplated herein such as those shown in U.S. Pat. No. 3,539,455 issued to Clark, Jr., the disclosure of which is expressly incorporated herein by reference.

Figure 14:
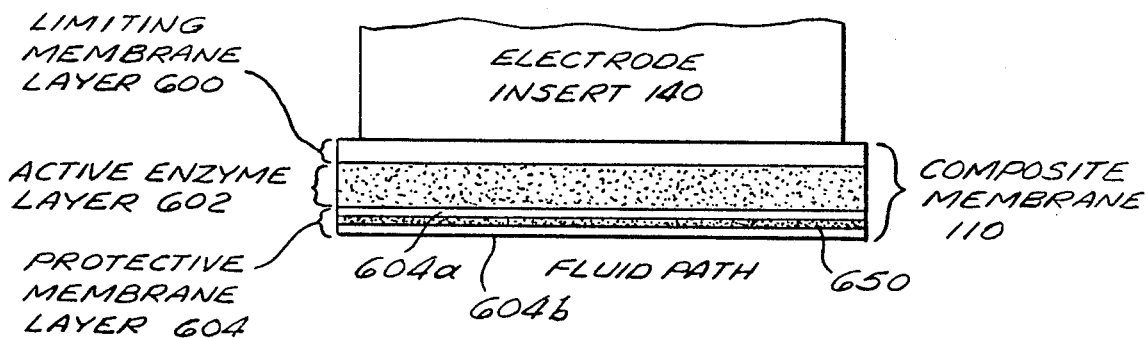
FIG. 14 is a schematic view of the multi-membrane layer(s) composite membrane of the present invention.

Referring to FIG. 14, the composite enzyme membrane 110 of the present invention is depicted. As shown, the composite membrane 110 is formed having a limiting membrane layer 600 disposed adjacent the electrode insert 140, an active enzyme membrane layer 602 and protective membrane layer 604. The protective membrane layer 604 is disposed on the exterior surface of the membrane 110 and is hence, first contacted by fluid flow through the recess 90 of the membrane gasket, i.e. either buffer aqueous solution, calibrant aqueous solution or body fluid sample.

With specific reference to a glucose enzyme membrane construction, the limiting membrane 600 is formed of a thin, polyester sheet having a thickness of approximately one thousandth of an inch. Preferably, the polyester sheet is micro-perforated by a conventional gamma radiation technique or a substitute technique therefor to possess a mean or average opening i.e. perforated pore size of approximately 0.1 micron diameter. The polyester sheet is preferably sprayed with a solution of cellulose acetate on one side thereof which travels through the openings in the perforated polyester sheet and forms a thin layer or coating thereon. The active enzyme membrane layer 602 comprises a glucose oxidase/bovine serum albumin solution cross-linked with gluteraldahyde which is applied as a bead and subsequently compressed to a thin film upon the limiting membrane 600. The glucose oxidase is therefore covalently linked to the bovine serum albumin thereby immobilizing the glucose oxidase and forming the enzyme layer 602.

Figure 14A:
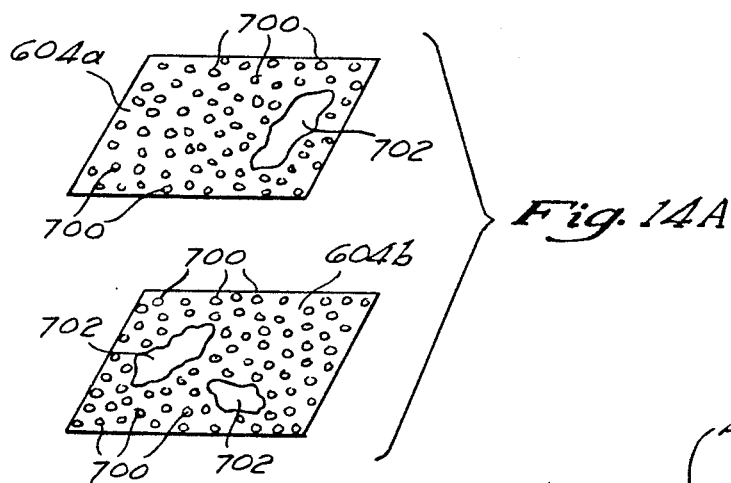
FIG. 14A is an exploded perspective view of the multiple layers of the protective membrane layer of the present invention.

The protective membrane layer 604 preferably comprises one or more thin sheets or layers of micro-perforated polycarbonate preferably having an average or mean pore size diameter of approximately 0.01 through 0.05 microns, which is applied over the active enzyme layer 602 and subsequently compressed thereagainst to form a composite membrane structure having a thickness of approximately 0.0015 inches. The Applicants have found that by utilizing two or three separate layers of polycarbonate upon the protective membrane layer, differences in the pore diameter size of the polycarbonate are compensated for resulting in an average pore or mean pore size of 0.01 micron in diameter. The function of this multi-layering of the polycarbonate sheet is schematically illustrated in FIG. 14A wherein two perforated polycarbonate sheets 604a and 604b are depicted. As shown, the micro-perforation of the sheets 604a and 604b typically results in a plurality of apertures 700 having a typical diameter of 0.01 through 0.05 microns. However, oftentimes the micro-perforation additionally causes minute tears or flaws 702 to be present which are interspersed throughout the apertures 700. Such flaws 702 would, of course, significantly affect the average perforation pore size diameter as well as the operation of the membrane layer 604.

By forming the protective layer 604 from multiple layers 604a, 604b, etc., which are laminated together, however, the possibility of the various flaws 702 being axially coincident with one another on adjacent layers 604a and 604b etc. is substantially eliminated, thereby resulting in a composite protective membrane layer 604 having an average pore size density of 0.01 through 0.05 microns and preferably 0.01 micron diameter. By selecting the average mean pore size diameter for the polycarbonate layers 604a and 604b, etc. which is advantageously achieved through utilizing multiple layers of polycarbonate for the protective membrane, the Applicants have found that the diffusion rate of glucose through the protective membrane layer 604 and into the active enzyme layer 602 can be controlled to insure that the rate at which the glucose is converted into a polargraphically detectable compound such as hydrogen peroxide within the active enzyme layer is linearly proportional to glucose concentration within desired residence time of the sample at the membrane.

Figure 14B:
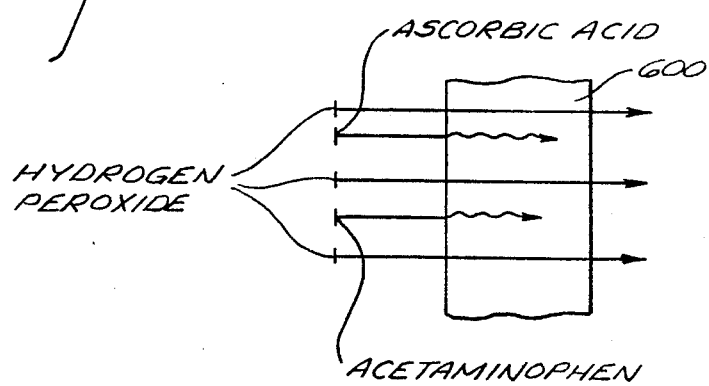
FIG. 14B is a schematic view of the difference in transport rates of substances through the limiting membrane layer of the present invention.

In operation, when glucose is presented at the outer surface of the composite membrane 110, either by way of a body fluid sample or by way of calibrant aqueous solution presented thereon, the protective membrane layer 604 serves to deter the enzyme layer 602 from peeling off the composite membrane structure and prevents the passage of blood cells and other particulate substances therethrough, as well as provides a controlled rate of passage of glucose into the active enzyme layer 602. In this regard, through system parameters of the present invention the rate at which glucose passes through the protective membrane layer 604 is adjusted by passage through the micron sized plural apertures 700 to achieve a linearly proportional relation between the signal generated by the electrode and glucose concentration. As the glucose diffuses into the active enzyme layer 602 at an adjusted or controlled rate, it is converted by the glucose oxidase enzyme to gluconic acid and hydrogen peroxide which travel through the active enzyme membrane layer 602 and into the limiting membrane layer 600. Due to the construction of the limiting membrane 600, the hydrogen peroxide is substantially free to travel therethrough so as to contact the electrode insert 140 while interfering low molecular weight substances such as acetaminophen and/or ascorbic acid are inhibited from passage through the limiting membrane layer. As will be recognized, such interfering substances such as acetaminophen and ascorbic acid could adversely affect the signal generated at the electrode and hence, the use of the limiting membrane to deter the passage of the same to the electrode is extremely desirable. In this regard, the Applicants have found that by use of a limiting membrane layer 600 constructed as defined herein, the passage of such interfering low molecular weight substances is inhibited for a time interval of approximately thirty seconds which, pursuant to system parameters of the present invention, is sufficient to enable accurate measurement and determination of the glucose concentration in the substance being measured. The manner in which this temporary screening is accomplished is illustrated schematically in FIG. 14B. As depicted, hydrogen peroxide generated at the active enzyme layer 602 along with interfering low molecular weight substances such as acetaminophen and/or ascorbic acid migrate by diffusion through the limiting membrane 600. However, hydrogen peroxide possesses a faster diffusion rate through the perforated polyester material of the limiting membrane 600 than does acetaminophen and/or ascorbic acid. As such, for relatively short time periods, due to the diffusion rate difference between hydrogen peroxide and acetaminophen and ascorbic acid through the layer 600, the limiting membrane 600 discriminates against such interfering substances and inhibits their passage to the electrode.

It will be recognized that the turnover rate, i.e. the rate at which the active enzyme layer 602 will convert glucose into a polarographically detectable substance such as hydrogen peroxide, is fixed for the particular active enzyme layer construction. As such, if the rate at which glucose enters the active enzyme membrane layer 602 is greater than the turnover rate of the enzyme layer 602, the hydrogen peroxide produced by the enzyme layer will not be linearly proportional to glucose concentration presented at the membrane, i.e. the enzyme layer 602 is only capable of converting glucose to hydrogen peroxide at the maximum rate for the enzyme layer.

In view of this recognition, the prior art has typically diluted the particular body fluid sample desired to be analyzed to insure that the turnover rate of the active enzyme membrane layer 602 is not exceeded. In contrast to the prior art teachings, the present invention specifically utilizes the protective membrane layer 604 which by controlling the pore size diameter of the micro-perforations 700 therein, the rate at which glucose passes through the protective membrane layer 604 and into the active enzyme layer 602 is maintained below the enzyme layer turnover rate.

In addition, to augment the adjustment capability of the protective membrane layer 604 for glucose measurement, the present invention further contemplates the use of immobilized catalase carried upon the protective membrane layer 604. Preferably, the catalase (designated by numeral 650 in FIG. 14) is immobilized upon one layer of the multi-layer protective membrane layer 604 by use of the previously described bovine serum albumin solution procedure and is disposed between adjacent layers 604a and 604b of the multi-layer protective membrane layer 604.

The catalase 650 serves to convert hydrogen peroxide to oxygen and water. The oxygen yielded by the catalase reaction is thereby present in an abundance or excess at the active enzyme membrane layer 602 and is capable of being utilized as a reactant by the active enzyme layer 602 reaction to insure that all the glucose is converted into gluconic acid and hydrogen peroxide.

As such, the excess oxygen, i.e. reactant formed by the catalase is extremely useful in the measurement of body fluid samples having abnormally high glucose concentrations which could drive the glucose reaction beyond acceptable levels at which enough oxygen is present at the enzyme layer 602 to produce a linearly proportional signal to glucose concentration. In this regard, the excess oxygen presented at the enzyme layer 602 via the catalase reaction insures that the electrode signal is linearly proportional to glucose concentration without the need of dilution of the body fluid sample.

ELECTRODE OPERATION

Figure 15:
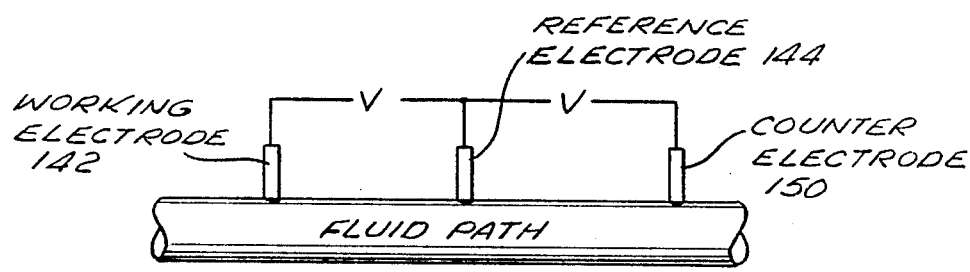
FIG. 15 is a schematic view of the voltages applied across the working electrode, reference electrode and counter electrode of the present invention.

As previously described, the working electrode 142, reference electrode 144 and counter electrode 150 are all disposed within the membrane fluid path and are electrically interconnected in a conventional manner to form in effect a Clark cell. In this regard, the principles of the Clark cell and polarographic/amperometric measurement techniques are well known to those having skill in the art. Basically, as a polarographically detectable substance such as hydrogen peroxide is generated from the enzyme reaction and contacts a working and reference electrode 142 and 144 respectively (shown in FIG. 15), the hydrogen peroxide readily depolarizes the polarographic anode, i.e. the working electrode 142 and current flow at a given applied voltage applied across the working electrode 142 and reference electrode 144 is directly proportional to the hydrogen peroxide concentration developed by the enzymatic chemical reaction adjacent the membrane. Thus, by measuring the current flow between the working electrode and reference electrode 144, an accurate determination of the glucose concentration of the solution being measured may be obtained. In addition, as is conventional for a Clark cell, an additional voltage is applied between the reference electrode 144 and counter electrode 150 to avoid degradation of the system.

In the preferred embodiment, the conventional electronic circuitry utilized to apply a voltage across the working electrode 142, reference electrode 144 and counter electrode 150 is carried upon the printed circuit board 152 disposed within the interior of the electrode carriage 60. Additionally in the preferred embodiment, the current signals generated in the working electrode 142 and reference electrode 144 circuit are converted to voltage signals by well known conventional techniques, which voltage signals are then amplified and processed by the processing and control electronics 24 of the overall analyzer device.

PSEUDO-RATE/CREATED PEAK MEASUREMENT TECHNIQUE

As is known to those having skill in the art, the conventional methods for following an enzyme reaction for the purposes of determining the concentration of a substance to be measured such as glucose comprise either a kinetic rate method or an end point method. In the kinetic rate method the maximum rate which the enzyme produces a polarographically detectable substance such as hydrogen peroxide is used or correlated with the concentration of glucose for measurement purposes. More simply stated, as the concentration of a substance like glucose increases, the enzyme response rate to that substance converts more of the glucose molecules per unit time than it would at a lower concentration of glucose. As such, in the kinetic rate measurement, the peak rate of enzyme conversion to hydrogen peroxide is located and utilized for measurement correlation purposes. This kinetic peak rate measurement technique is extremely temperature dependent and further, requires precise monitoring of the electrical signals generated across the working and reference electrodes in order to accurately recognize the kinetic peak rate measurement interval.

As opposed to the kinetic rate method, the end point method does not identify the fastest rate for the enzyme reaction but rather, allows the enzyme reaction to reach a final maximum conversion rate per unit time. Although the identification of the maximum rate of reaction through the end point method is more easily determinable or identifyable, it requires a substantial time period in most instances to achieve the desired end point measurement value. Further, such end point measurement technique is extremely deficient in recovery time thereby detracting from its use when sequential multiple measurements are desired to be accomplished utilizing the same enzyme membrane.

Although the subject invention may utilize either the kinetic rate method or end point method, the present invention specifically addresses the deficiencies between the kinetic rate and end point prior art measurement techniques by creating a novel pseudo-rate/-created peak measurement technique for an enzyme reaction. In this regard, the subject Applicants specifically define the chemistry of the composite membrane 110 and engineer the operation of the resident times of the buffer and calibrant aqueous solutions and body fluid sample upon the membrane to drive the natural kinetics of an enzyme reaction and allow rapid identification of desired measurement data.

More particularly, as previously described, the composite membrane layer 110 is specifically defined to include a protective membrane layer 604 which adjusts the rate at which the substance desired to be measured, such as glucose, travels into the active enzyme layer 602 as well as insures that sufficient oxygen is present at the active enzyme layer 602 such that a linear rate of conversion of the glucose concentration to hydrogen peroxide sensed at the electrode is achieved. With this linear rate of the enzyme reaction insured, the resident time during which the glucose bearing calibrant aqueous solution and/or glucose bearing body fluid sample is disposed upon the membrane is precisely controlled or selected. This control is obtained by the selected introduction of the non-glucose bearing buffer aqueous solution to the membrane which causes a reverse diffusion direction of glucose across the enzyme layer which is readily identifiable by a decreasing voltage signal developed across the working and reference electrodes.

Figure 16:
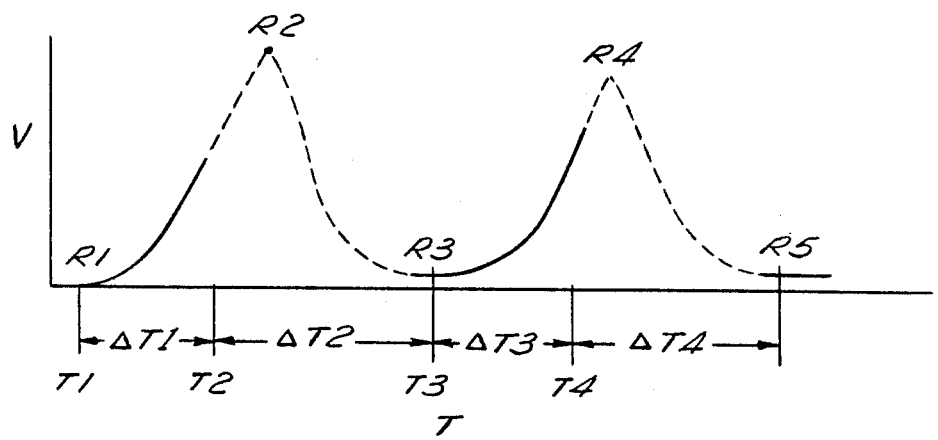
FIG. 16 is a graph depicting the pseudo-rate/created peak measurement technique of the present invention.

A graphic illustration of the pseudo-rate/created peak measurement techinque of the present invention is illustrated in FIG. 16 wherein voltage signal values generated across the working and sensor electrodes is depicted on the vertical scale and time is depicted on the horizontal scale of the graph. Initially, the pseudo-rate/created peak measurement technique contemplates the buffer aqueous solution which preferably does not contain any glucose therein, to be presented to the membrane wherein a voltage value designated as R1 in FIG. 16 is obtained. Between time interval Delta T1, a quantity of calibrant aqueous solution is drawn through the interior of the probe 40 and presented to the membrane 110 wherein the voltage value developed across the working and reference electrode increases as illustrated in FIG. 16. At time T2, an additional quantity of buffer aqueous solution (not containing any glucose therein) is again drawn through the interior of the probe 40 to be disposed at the membrane. In view of the travel time required to transport the buffer aqueous solution through the interior of the probe 40 to be presented at the membrane, during the initial period of the buffer solution flow, the voltage values generated across the working and reference electrode continue to increase as depicted by the dotted line in FIG. 16. When the buffer aqueous solution reaches the membrane, the diffusion rate of glucose across the enzyme layer 602 of the composite membrane 110 or, more particularly, the diffusion direction will reverse, wherein a decline of the voltage values generated across the reference and working electrode results. This artificially created peak voltage value is represented by the designation R2 in FIG. 16. The flow of the buffer aqueous solution continues through a time period designated Delta T2, wherein the voltage value will decrease toward the voltage value of R1. When the voltage value approximates the value R1, i.e. is within a preselected specified tolerance of the voltage value R1, an additional voltage value reading R3 is taken. At this time designated as T3, a quantity of the body fluid sample desired to be measured is transported through the interior of the probe 40, which flow will be maintained through a time period designated as Delta T3. As depicted in FIG. 16, the voltage values generated across the electrode will subsequently increase. At the expiration of the time period Delta T3, i.e. at time T4, another quantity of buffer aqueous solution is again supplied through the interior of the probe 40 wherein upon reaching the composite membrane 110, a reverse diffusion rate of glucose across the enzyme layer 602 again occurs, resulting in a peak voltage value R4 to be observed at time T5. Continued resident time of the buffer aqueous solution upon the membrane results in a decrease of the voltage value after time T5 as illustrated in FIG. 16.

As will be recognized, by observing the voltage values R1, R2, R3, and R4, and by further knowing that R2 represents a known concentration glucose calibrant solution, the concentration of the glucose concentration contained within the body fluid sample can be determined by the mathematical equation:

$$\frac{R4 - R3}{R2 - R1} \times \text{constant} = \text{Concentration of Glucose in Body Fluid Sample}$$

where the constant is the known concentration of glucose in the calibrant aqueous solution.

As will be recongnized, by the pseudo-rate/created peak measurement technique of the present invention, the peak voltages R2 and R4 are artificaly created by the selective and timed introduction of the buffer aqueous solution which results in a reverse diffusion direction across the membrane which further, is easily detectable by monitoring the voltage values generated across the working and reference electrodes. In addition, sampling of data to determine the created peak voltage values R2 and R4 need only be initiated during a relatively short period of time between the beginning of the introduction of the buffer aqueous solution flush periods, i.e. Delta T2 and Delta T4, thereby maintaining the data storage parameters and software parameters at a minimum. Finally, due to the introduction of the buffer aqueous solution after the introduction of the body fluid sample to the membrane, the recovery time for the enzyme membrane to enable repeated measurements is substantially reduced.

DETAILED OPERATION OF THE ENZYMATIC ELECTRODE

With the structure and principles of the present invention defined, the operation of the enzymatic electrode with specific reference to the measurement of glucose in a blood sample on the medical analyzer device 10 may be described. It will be recognized that the operation of the enzymatic analytical module or work station 33 is controlled by the processing and control electronics (not shown) of the medical analyzer device 10 which is disclosed in pending U.S. patent application Ser. No. 798,791. The processing and control electronics disclosed in said pending application include a preferred program of operation stored in the microprocessor of the same. With specific relation to the subject invention, when the enzymatic analytical module 33 of the present invention is disposed within the medical analyzer device 10, substitute programs of operation are utilized to allow the microprocessor of the processing and control electronics to sequence the operation of the probe drive mechanism 16, fluidic pump and vacuum system 22, electrode circuitry contained upon the printed circuit board 152 and storage and data processing requirements for the enzymatic electrode module of the present invention. A detailed listing of that substitute program is set forth in the MICROFICHE APPENDIX to this specification. A physical description of the sequencing of operations of the subsystems follows herebelow and is schematically depicted in relation to probe movements in FIGS. 17 through 21.

Figures 17, 18, 19, 20, 21:
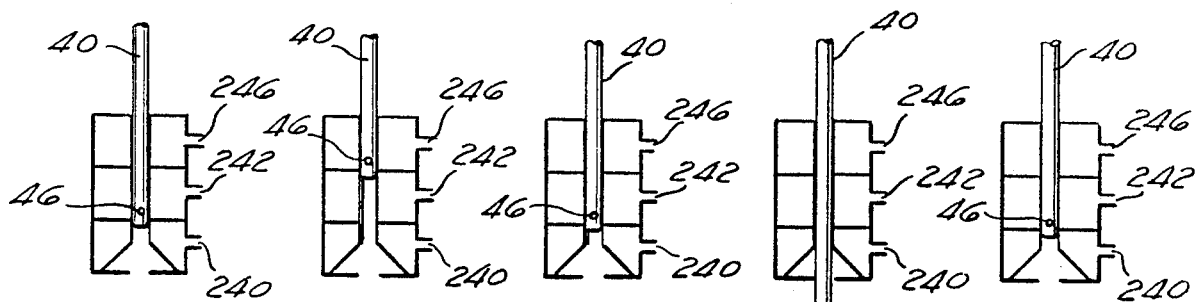
FIGS. 17 through 21 are schematic views illustrating the sequential steps of the probe during a measurement procedure.

In operation, the probe 40 is normally maintained in a "home" position wherein the inlet port 46 disposed adjacent the lower end of the probe 40 is disposed within the central region of the wash cell 18 adjacent the aperture 242 of the wash cell 18 as depicted in FIG. 17. As will be recognized, in this home position through either initial purging of the system or previous measurement operation of the same, the probe membrane flow path defined by the interior of the probe 40, aperture 92, recess 90 and aperture 94 of the membrane gasket 80, and interior of the counter electrode 150 contains a quantity of the buffer aqueous solution therein. This quantity of buffer aqueous solution which preferably does not contain any glucose therein serves to continuously maintain the composite membrane 110 in an aqueous bath which serves to purge any residual glucose from the composite membrane 110.

To initiate a desired test or measurement procedure upon the enzyme analytical module 33, a body fluid sample such as blood, serum or plasma must be extracted from a patient in conventional manner and inserted into the interior of the sample cup 302. The sample cup 302 is then positioned upon the sample cup shelf 306 of the analytical module 33 so as to axially align the interior of the sample cup 302 with the probe 40 of the module 33. Activation of the "test request" switch 440 disposed on the upper frontal portion of the module 33 as described in pending U.S. patent application Ser. No. 798,791, causes the processing and control electronics to identify the particular enzymatic electrode module 33 for which a test procedure is desired and facilitate operation of its respective subassemblies 14 through 22.

Initially the probe drive mechanism 16 is activated to raise the probe 40 upwardly within the wash cell 18 such that the inlet port 46 of the probe 40 is disposed in the uppermost region of the wash cell 18 (as depicted in FIG. 18) wherein the calibrant aqueous solution supplied via the conduit 534 to the uppermost region of the wash cell is presented at the inlet 46. As will be recognized, the location of the probe 40 at this position is verified by the interaction of the optical sensing systems 416 and 418 and flag 412 of the module 33. Disposed in this stationary position, the fluidic pump and vacuum system 22 is intiated, whereby due to the vacuum applied to the inward end of the counter electrode 150, a quantity of calibrant aqueous solution which in the preferred embodiment comprises an aqueous solution having a known concentration of glucose, i.e. the substance desired to be measured, is transported upwardly through the inlet 46 of the probe 40 and through the membrane flow path so as to be disposed at the composite membrane 110. In the presently preferred embodiment, this flow of calibrant aqueous solution is initiated for a time sufficient to insure that the calibrant aqueous solution reaches the membrane 110 and displaces all buffer aqueous solution previously disposed at the membrane, which normally takes three to five seconds in duration. Simultaneous with the transport of the calibrant aqueous solution through the probe, operation of the fluidic pump and vacuum system 22 causes a quantity of buffer aqueous solution to be pumped through the central region of the wash cell 18 downwardly into the lower region of the wash cell 18 wherein it is removed therefrom by the vacuum being applied via the port 232 and returned to the waste storage reservoir 500. As will be recognized, this flow of buffer aqueous solution thoroughly cleans the central and lower regions of the wash cell of any residual body fluid sample or the like accumulating within the central and lower regions of the wash cell 18. Subsequently, the operation of the fluidic pump and vacuum system 22 is discontinued wherein the calibrant aqueous solution disposed at the membrane 110 is allowed to incubate or be resident upon the membrane 110 for a period of time, typically comprising an additional five to ten second period.

During this resident period, the voltage value generated across the working and reference electrodes begins rising from its R1 value toward an R2 value as depicted in FIG. 16 and the probe drive mechanism is again initiated causing the probe to reciprocate axially downward from the uppermost region from the wash cell 18 to the central region of the wash cell 18 as depicted in FIG. 19 wherein the inlet of the probe 46 is again disposed in the central region of the wash cell 18 so as to be in flow communication with the buffer aqueous solution presented at the aperture 242. As will be recognized, during downward reciprocation of the probe 40 within the wash cell 46, passage of calibrant aqueous solution from the upper region of the wash cell to the middle or lower region of the wash cell is prevented by the dynamic seal formed by the O-ring 214 against the exterior of the probe 40.

At the end of this resident period for the calibrant solution upon the membrane 110, i.e. at time T2 in FIG. 16, the fluidic pump and vacuum system 22 is reinitiated wherein a quantity of buffer aqueous solution is drawn from the wash cell 18 through the inlet 46 of the probe 40 and through the membrane flow path. This flow is maintained for a sufficient period of time to completely flush or purge the membrane flow path of all calibrant solution therefrom wherein the membrane 110 and all electrodes are disposed within the buffer aqueous solution. Simultaneous with the initiation of this purge or flush cycle, the processing and control electronics begin sampling voltage values generated across the working and reference electrodes and when the microprocessor obtains five consecutive negative or decreasing voltage values from the electrodes, the voltage value just prior to the first one of the decreasing voltage values is stored in the memory of the microprocessor representing the calibrant peak value R2 in FIG. 16.

As previously discussed, the occurrence of the decreasing voltage value during this sampling of data represents the reverse diffusion direction of glucose across the membrane from the electrode to the buffer aqueous solution. After a sufficient resident time of the buffer aqueous solution upon the membrane 110, the fluidic pump and vacuum system 22 is deactivated and the probe drive mechanism 16 is activated to cause the probe 40 to reciprocate axially downward through the lower open end of the wash cell 18 and into the sample cup 302 as depicted in FIG. 20.

When the voltage value generated across the reference and working electrode degrades to within specified tolerances of the original voltage value R1 of the buffer solution upon the membrane 110, an additional voltage reading R3 is taken, i.e. stored which represents the new baseline of the electrode voltage signal. At this time designated as T3 in FIG. 16, the fluidic pump and vacuum system 22 is reinitiated to cause a quantity of the body fluid sample desired to be measured to be drawn upwardly from the sample cup within the inlet 46 of the probe 40 and into the membrane flow path. The flow of body fluid sample from the sample cup 302 is maintained for a sufficient period of time to insure that all of the buffer solution maintained within the membrane flow path is purged from the vicinity of the composite membrane 110 and that the blood sample is disposed within, i.e. completely occupies, the entire membrane flow path. Typically this period of time is approximately three to five seconds and after completion of the same, the fluidic pump and vacuum system 22 is deactivated to allow the body fluid sample to incubate upon the membrane 110. During the drawing of the body fluid sample upwardly within the probe, buffer aqueous solution is simultaneously pumped through the central and lower region of the wash cell 18 and removed by vacuum at the port 240 and returned to the swaste reservoir. During this incubation period, which preferably comprises five to ten seconds, the voltage signal generated across the working and sensor electrodes begins to increase as depicted in FIG. 16, rising toward the value R4 and the probe drive mechanism 16 is again initiated causing the probe 40 to be reciprocated axially upward out of the sample cup 20 and back to the "home" position depicted in FIG. 21. In this "home" position the probe inlet 46 is again disposed within the central or midportion of the wash cell 18 so as to be in flow communication with the buffer aqueous solution presented at the port or aperture 242.

After a sufficient incubation period of the body fluid sample upon the electrode 110, i.e. at time T4 in FIG. 16, the fluidic pump and vacuum system 22 is again temporarily initiated causing buffer aqueous solution to travel through the inlet port 46 of the probe 40 and through the membrane flow path so as to purge all body fluid sample therefrom and represent buffer aqueous solution at the membrane 110. Simultaneous with the initiation of this purge cycle, voltage signal data is sampled from the working and reference electrodes by the microprocessor. In view of the travel time required for the buffer aqueous solution to travel upwardly through the probe 40 so as to be disposed upon the membrane 110, during the initial flushing cycle the voltage value across the electrodes continues to rise until a reverse diffusion direction of glucose across the membrane is again achieved. When five consecutive decreasing voltage values are recognized by the microprocessor, the voltage value just prior to the first of the decreasing voltage values represented by the number R4 in FIG. 16 is stored. Through continued residence of the buffer solution upon the membrane, as an additional baseline FIG. R5 is obtained for the voltage value across the electrodes wherein a repeat of the cycle previously described for a new body fluid sample may be initiated.

Upon obtaining and storing the R4 value, the system software causes the microprocessor to initiate calculation functions wherein the values of R1, R2, R3 and R4, as well as the particular glucose concentration constant of the calibrant aqueous solution utilized in the test are processed in a manner previously described to derive a resultant glucose concentration value for the body fluid sample measured in the test sequence, which resultant value is output on the display of the medical analyzer device 10.

As will be recognized, due to the intermittent flow of buffer aqueous solution through the central and lower regions of the wash cell, the lower region of the wash cell serves to strip or remove any residual portion of the body fluid sample from the end of the probe 40. Further, due to the frustro-conical shaped configuration of the lower opening of the wash cell 18, any air bubbles trapped upon the exterior of the probe 40 are separated or removed therefrom and prevented from passing into the central or midportion of the wash cell 18. Further, due to the frustro-conical shaped aperture, this stripping of air bubbles and residual body fluid is accomplished without disturbing the fluid meniscus existing at the inlet 46 of the probe 40.

From the above description it will be recognized that the present invention provides an automatic determination of the concentration of a polarographically detectable substance contained within a body fluid sample in a rapid and efficient manner. Further, it should be recognized that these accurate measurements are effectuated without the use of complicated thermostatic temperature control systems and further, without diluting the body fluid sample. This is made possible by the rapid and simple manipulation of the probe between the wash cell and an unknown body fluid specimen in a simple vertical axial motion which permits the aqueous solutions and body fluid data samplings to be effectuated in relatively close time proximity. Further, due to the relatively large thermal mass of the probe 40 compared to the extremely small volume of body fluid sample and the probe 40 normally being resident in the "home" position in the buffer aqueous solution in the wash cell at ambient temperature, upon rapid immersion within the sample cup, the probe serves to immediately equalize the temperature of the body fluid sample to the temperature of the probe, which temperatue is substantially equal to the temperature of the buffer aqueous solution and/or calibrant aqueous solution contained within the wash cell. Due to the temperature of the calibrant aqueous solution and buffer aqueous solution within the wash cell being equal to the temperature of the body fluid sample when the probe is rapidly immersed in the sample, inaccuracies caused by the temperature differential between such aqueous solutions and the specimen is eliminated.

In addition, although for purposes of explanation, the particular enzymatic electrode and enzymatic analytical module disclosed herein has been described in relation to obtaining glucose measurements, the substitution of an appropriate enzyme layer in the composite enzyme membrane structure as well as the substitution of appropriate buffer and calibrant solutions therefor, will permit the present invention to be utilized to determine the concentration of other detectable substances in whole blood such as creatinine, triglyceride, cholesterol, ascorbic acid, amino acid, lactose, galactose, and other substances, all of which are expressly contemplated herein.

What is claimed is:

1. An enzymatic sensor assembly for use in an analyzer device comprising:
    a membrane chamber having an inlet and outlet;
    an enzyme bearing membrane disposed within said membrane chamber between said inlet and outlet;
    a sensor disposed within said membrane chamber and located on one side of said membrane;
    a membrane holder sized to carry said membrane, said holder formed to releasably mount said membrane within said membrane chamber adjacent said sensor and define on the opposite side of said membrane a fluid flow path within said membrane chamber between said inlet and outlet; and
    a gasket insertable within said membrane holder to form a fluid-tight seal between said membrane holder and said membrane chamber, wherein the fluid flow path comprises a flow channel formed in said gasket.

2. The enzymatic sensor assembly of claim 1 wherein said membrane is mounted within said gasket and positioned adjacent said flow channel.

3. The enzymatic sensor assembly of claim 2 wherein said gasket is formed having a complementary shaped aperture sized to receive a portion of said sensor therein and maintain said membrane in tension against said sensor.

4. The enzymatic sensor assembly of claim 3 wherein said sensor comprises an electrode.

5. The enzymatic sensor assembly of claim 4 wherein said sensor comprises a working electrode and a reference electrode.

6. The enzymatic sensor assembly of claim 5 further comprising a counter electrode in fluid communication with said flow channel formed in said gasket.

7. The enzymatic sensor assembly of claim 6 wherein said counter electrode comprises a tubular member.

8. The enzymatic sensor assembly of claim 7 further comprising a probe carried by said membrane chamber for introducing fluid into said inlet.

9. The enzymatic electrode of claim 8 wherein said probe comprises a tubular member having a closed first end, an open second end communicating with said inlet of said membrane chamber and an aperture formed adjacent said closed end for receiving fluid therethrough.

10. The enzymatic sensor assembly of claim 9 wherein said membrane holder and said membrane chamber are formed in a complementary configuration.

11. The enzymatic sensor assembly of claim 10 wherein opposite ends of said membrane chamber are formed in differing configurations to prevent improper mounting of said membrane holder to said membrane chamber.

12. An enzymatic electrode comprising:
    a membrane chamber;
    an enzyme bearing membrane disposed within said chamber;
    an electrode positioned to contact said membrane on one side thereof and generate a signal in response to the presence of an enzyme reaction occurring at said membrane;
    a probe in flow communication with said membrane chamber for transporting fluids through said membrane chamber;
    a wash cell formed to store in a segregated manner a first and second aqueous solution;
    a sample cup sized to store a quantity of a fluid specimen therein;

means for selectively reciprocating said probe between said wash cell and said sample cup;

means for intermittently transferring said first and second aqueous solutions and said fluid specimen through said probe and said membrane chamber when said probe is disposed in said wash cell and said sample cup; said membrane chamber and said electrode being supported upon a carriage adapted to reciprocate with said probe during reciprocal movement of said probe between said wash cell and sample cup, said electrode comprising an electrode insert mounted to said carriage having a working electrode and a reference electrode;

a printed circuit board positioned in said carriage adapted to frictionally receive a portion of said working and reference electrodes therein to form an electrical interface between said working and reference electrodes; and a counter electrode supported by said carriage, said counter electrode forming a fluid outlet for said membrane chamber and extending through said printed circuit board to be electrically interfaced to said working and reference electrode.

13. An enzymatic electrode comprising:
a membrane chamber;
an enzyme bearing membrane disposed within said chamber;
an electrode positioned to contact said membrane on one side thereof and generate a signal in response to the presence of an enzyme reaction occurring at said membrane;
a probe in flow communication with said membrane chamber for transporting fluids through said membrane chamber;
a wash cell formed to store in a segregated manner a first and second aqueous solution;
a sample cup sized to store a quantity of a fluid specimen therein;
means for selectively reciprocating said probe between said wash cell and said sample cup;
means for intermittently transferring said first and second aqueous solutions and said fluid specimen through said probe and said membrane chamber when said probe is disposed in said wash cell and said sample cup; said membrane chamber and said electrode being supported upon a carriage adapted to reciprocate with said probe during reciprocal movement of said probe between said wash cell and sample cup, said electrode comprising an electrode insert mounted to said carriage, wherein said wash cell is disposed at a vertical elevation between said sample cup and said membrane carriage.

14. The enzymatic electrode of claim 13 wherein said wash cell includes an aperture sized to permit said probe to be reciprocated therethrough, said aperture being segregated into plural axially separated regions.

15. The enzymatic electrode of claim 14 wherein a first one of said plural axially separated regions stores said first aqueous solution and a second one of said plural axially separated regions stores said second aqueous solution.

16. The enzymatic electrode of claim 15 wherein a third one of said plural axially separated regions includes means for supplying a vacuum to said probe.

17. The enzymatic electrode of claim 16 wherein said third one of said plural axially separated regions is formed in a frustro-conical shaped configuration.

18. The enzymatic electrode of claim 17 further comprising means for sensing the axial position of said probe within said wash cell and said sample cup.

19. The enzymatic electrode of claim 18 further comprising a membrane holder sized to receive said membrane therein and releasably mount said membrane within said membrane chamber.

20. An enzymatic electrode comprising:
a membrane chamber;
an enzyme bearing membrane mounted within said chamber;
a membrane holder formed to carry said membrane and define a fluid flow path extending on one side of said membrane for transporting a fluid across said membrane;
a sensor electrode and a reference electrode disposed on the other side of said membrane; and
a counter electrode in fluid communication with said fluid flow path.

21. The enzymatic electrode of claim 20 wherein said counter electrode comprises a tubular member forming the outlet of said fluid flow path.

22. The enzymatic electrode of claim 21 wherein said membrane is releasably mounted within said membrane chamber.

23. The enzymatic electrode of claim 22 wherein said membrane holder is formed to receive said membrane therein, said membrane holder releasably mounted to said membrane chamber.

24. The enzymatic electrode of claim 22 wherein said sensor electrode and reference electrode are disposed in an insert extending into said membrane chamber.

25. The enzymatic electrode of claim 24 further comprising a fluid conducting probe mounted to said membrane chamber having an inlet adjacent one end and an outlet at the opposite end communicating with said fluid flow path.

26. The enzymatic electrode of claim 25 wherein said fluid flow path comprises a channel formed in a gasket positioned within said membrane holder.

27. The enzymatic electrode of claim 26 wherein said membrane is mounted within an aperture formed within said gasket.

28. The enzymatic electrode of claim 27 wherein said membrane comprises a composite, multi-layer membrane.

29. A composite enzymatic membrane comprising:
a first membrane layer having a stabilized active enzyme for converting a desired substance of interest into a detectable substance;
a second membrane layer disposed on one side of said first membrane layer formed to inhibit the passage therethrough of substances which interfer with the measurement of said detectable substance; and
a third membrane layer disposed on the opposite side of said first membrane layer to adjust the diffusion rate of said desired substance of interest into said first membrane layer and generate a reactant utilized by said stabilized active enzyme in converting the desired substance of interest into the detectable substance.

30. The composite enzymatic membrane of claim 29 wherein said third membrane layer comprises a micro-perforated layer of sheet material.

31. The composite enzymatic membrane of claim 30 wherein said third membrane layer comprises a plurality of micro-perforated layers of sheet material.

32. The composite enzymatic membrane of claim 31 wherein said plurality of micro-perforated layers of sheet material carry catalase thereon.

33. A composite enzymatic membrane for use in a measurement sensor comprising:
   a first membrane layer having a stabilized active enzyme for generating a measurable substance at a sensor in response to an analyte enzyme reaction; and
   a second membrane layer positioned on one side of said first membrane layer formed to adjust the transport rate of an analyte into said first membrane layer to linearize the signal generated by the sensor, said second membrane layer including means for generating a reactant utilized by said stabilized active enzyme in the analyte enzyme reaction.

34. The composite enzymatic membrane of claim 33 wherein said second membrane layer comprises a micro-perforated layer of sheet material.

35. The composite enzymatic membrane of claim 34 wherein said second membrane layer comprises a plurality of micro-perforated layers of sheet material.

36. The composite enzymatic membrane of claim 34 further comprising a third membrane layer positioned on the other side of said first membrane layer for inhibiting the passage therethrough of substances which would interfer with the measurement of said measureable substance at the sensor.

37. A wash cell for an enzymatic electrode probe comprising:
   a vessel having an aperture extending therethrough sized to permit axial reciprocation of a probe therethrough;
   means disposed within said vessel for axially segregating said vessel into at least two distinct chambers, each formed to maintain a first and second aqueous solution; and
   means disposed within said vessel and about said aperture for forming a static seal between said at least two distinct chambers and a dynamic seal between said probe and said vessel during reciprocation of said probe through said vessel, wherein said seal forming means comprises a spacer spool positioned in said aperture at the upper one of said at least two chambers having a pair of O-rings disposed on opposite ends thereof.

38. The wash cell of claim 37 further comprising a retainer plate insertable within said vessel at an axial position to abut one of said pair of O-rings and exit a compressive force thereagainst.

39. The wash cell of claim 38 wherein said means disposed within said vessel axially segregates said vessel into three distinct chambers.

40. The wash cell of claim 39 wherein said third distinct chamber is disposed axially below said first and second chambers and is formed to supply a vacuum within said third chamber to clean said probe during reciprocation therethrough.

41. A composite enzymatic membrane for use in measuring glucose concentrations in a body fluid sample comprising:
   a first membrane layer having immobilized glucose oxidase carried thereon;
   a second membrane layer comprising a micro-perforated polyester sheet disposed on one side of said first membrane layer defining means to prevent the passage of measurement interfering substances therethrough; and
   a third membrane layer disposed on the opposite side of said first membrane layer defining means for adjusting the diffusion rate of glucose into said first membrane layer.

42. The composite enzymatic membrane of claim 41 wherein said third membrane layer comprises a micro-perforated polycarbonate sheet.

43. The composite enzymatic membrane of claim 42 wherein said third membrane layer comprises a plurality of micro-perforated polycarbonate sheets.

44. The composite enzymatic membrane of claim 43 wherein said third membrane layer further includes an immobilized catalase positioned between adjacent ones of said plurality of micro-perforated polycarbonate sheets.

* * * * *